United States Patent
Zucherman et al.

(10) Patent No.: US 8,123,752 B2
(45) Date of Patent: Feb. 28, 2012

(54) SYSTEMS AND METHODS FOR INJECTING BONE FILLER INTO THE SPINE

(75) Inventors: James F. Zucherman, San Francisco, CA (US); Ken Y. Hsu, San Francisco, CA (US)

(73) Assignee: Spartek Medical. Inc., Concord, CA (US)

( * ) Notice: Subject to any disclaimer, the term of this patent is extended or adjusted under 35 U.S.C. 154(b) by 241 days.

(21) Appl. No.: 12/690,874

(22) Filed: Jan. 20, 2010

(65) Prior Publication Data

US 2010/0191297 A1    Jul. 29, 2010

Related U.S. Application Data

(60) Provisional application No. 61/146,992, filed on Jan. 23, 2009.

(51) Int. Cl.
*A61F 2/46* (2006.01)
(52) U.S. Cl. ...................................................... 606/86 R
(58) Field of Classification Search ................ 606/86 R, 606/151, 155
See application file for complete search history.

(56) References Cited

U.S. PATENT DOCUMENTS

| | | | |
|---|---|---|---|
| 5,725,582 A | 3/1998 | Bevan et al. | |
| 6,066,142 A | 5/2000 | Serbousek et al. | |
| 6,261,296 B1 | 7/2001 | Aebi et al. | |
| 6,342,056 B1 | 1/2002 | Mac-Thiong et al. | |
| 6,364,883 B1 | 4/2002 | Santilli | |
| 6,695,842 B2 | 2/2004 | Zucherman et al. | |
| 6,699,246 B2 | 3/2004 | Zucherman et al. | |
| 6,726,691 B2 | 4/2004 | Osorio et al. | |
| 6,814,736 B2 | 11/2004 | Reiley et al. | |
| 6,899,719 B2 | 5/2005 | Reiley et al. | |

(Continued)

FOREIGN PATENT DOCUMENTS

WO   WO 2006/017641 A2   2/2006

OTHER PUBLICATIONS

Advanced Biomaterial Systems, retrieved from: http://www.im-medica.com/, accessed on Aug. 14, 2006, 17 pages.

(Continued)

*Primary Examiner* — Anu Ramana
(74) *Attorney, Agent, or Firm* — Fliesler Meyer LLP

(57) ABSTRACT

A method for strengthening a spinous process comprises positioning a framework over an outer surface of the spinous process, the framework comprising a mesh connected to a frame. Bone filler is distributed over the mesh so that the bone filler contacts the mesh and contacts the spinous process. The bone filler is allowed to cure. A jig is positioned at the spinous process so that a slot through the jig is exposed to a side of the spinous process. A cannula is oriented so that the cannula is receivable in the slot, and insertable into the spinous process through the slot. Bone filler is injected into the spinous process by way of the cannula, with the injection terminating when a desired amount of bone filler has been injected into the spinous process. The cannula is then removed and the bone filler allowed to cure within the vertebra. The above steps can also be accomplished simultaneously or in any order. Further, bone filler injected into the spinous process can also contact the mesh as the bone filler passes at least partially through the spinous process.

28 Claims, 18 Drawing Sheets

U.S. PATENT DOCUMENTS

| | | | |
|---|---|---|---|
| 6,908,506 | B2 | 6/2005 | Zimmermann |
| 7,022,082 | B2 | 4/2006 | Sonek |
| 7,029,473 | B2 | 4/2006 | Zucherman et al. |
| 7,048,736 | B2 | 5/2006 | Robinson et al. |
| 7,611,526 | B2 * | 11/2009 | Carl et al. .................. 606/248 |
| 7,892,246 | B2 * | 2/2011 | Akin et al. .................. 606/155 |
| 2005/0208094 | A1 | 9/2005 | Armitage et al. |
| 2006/0036246 | A1 | 2/2006 | Carl et al. |
| 2006/0036256 | A1 | 2/2006 | Carl et al. |
| 2006/0036259 | A1 | 2/2006 | Carl et al. |
| 2006/0036323 | A1 | 2/2006 | Carl et al. |
| 2006/0036324 | A1 | 2/2006 | Sachs et al. |
| 2006/0041311 | A1 | 2/2006 | McLeer |
| 2006/0058790 | A1 | 3/2006 | Carl et al. |

OTHER PUBLICATIONS

Anderson, Paul A., et al., "Treatment of Neurogenic Claudication by Interspinous Decompression: Application of the X STOP Device in Patients with Lumbar Degenerative Spondylolisthesis," Journal of Neurosurgery: Spine, Jun. 2006, pp. 463-471, vol. 4.

Cardinal Health, "Focusing on the Procedure, not the Clock. Ava-Tex Radiopaque Bone Cement for Vertebroplasty", retrieved from: http://www.carefusion.com/images/AVAtex_Brochure.pdf, 10 pages.

Biomet Europe, "Biomet Bone Cement V. Vertebroplasty Bone Cement", retrieved from: http://www.bonecement.com/index.php?id=15109, accessed on Aug. 14, 2006, 8 pages.

Medcompare, "Orthopedics Product Matrix: Bone Cement", retrieved from: http://medcompare.com/matrix/1635/Bone-Cement.html, accessed on Aug. 14, 2006, 4 pages.

Lam, Sandi, et al., "A Novel Percutaneous System for Bone Graft Delivery and Containment for Elevation and Stabilization of Vertebral Compression Fractures," Neurosurgery Focus, Mar. 2005, 7 pages, vol. 18(3):E10.

Komath, Manoj, et al., "Development of a Fully Injectable Calcium Phosphate Cement for Orthopedic and Dental Applications," Bull. Mater. Sci., Jun. 2003, pp. 415-422, vol. 26, No. 4.

Palussiere, Jean, et al., "The Clinical Use of Cortoss Synthetic Bone Void Filler in the Repair of Fractures in the Vertebral Body," pp. 151-158.

Parmar, Vikram, et al., "Surgical Treatment of Axial Back Pain", retrieved from: http://www.spine-dr.com/site/pdf/Axial_Back_Pain_Treatment.pdf, 53 pages.

Disc-O-Tech, "Confidence High Viscosity Bone Cement—FDA and CE Approved for Marketing", retrieved from: http://www.disc-o-tech.com, accessed on Aug. 14, 2006, 4 pages.

Exactech, "Bone Cement", retrieved from: http://www.exac.com, accessed on Aug. 14, 2006, 12 pages.

St. Francis Medical Technologies, Inc., "X STOP Interspinous Process Distraction for Intermittent Neurogenic Claudication," Business Briefing: Global Surgery, 2003, 3 pages.

Somatex® Medical Technologies GmbH, "ASPI-CUT® Punktionsnadel / Puncture Needle", retrieved from: http://www.somatex.com, 2 pages.

Somatex® Medical Technologies, "BIOPSIE / BIOPSY: Transplant—Aspirationsnadel / Transplant—Aspiration Needle", retrieved from: http://www.somatex.com, 2 pages.

Kasperk, Christian, et al., "Treatment of Painful Vertebral Fractures by Kyphoplasty in Patients with Primary Osteoporosis: A Prospective Nonrandomized Controlled Study," Journal of Bone and Mineral Research, 2005, pp. 604-612, vol. 20, No. 4.

Kryptonite, "Why is Kryptonite the PMMA Alternative?", retrieved from: http://www.kryptoniteusa.com/, accessed on Aug. 14, 2006, 4 pages.

Kyphon, Inc., "High-Viscosity Radiopaque Bone Cement", Kyphx® HV-R, retrieved from: http://www.kyphon.com, 10 pages.

Kyphon, Inc., "The Fracture Line", retrieved from: http://www.kyphon.com/us/home.aspx?siteid=1, Winter 2005, 4 pages, vol. 2, No. 2.

Cassak, David, "St. Francis Medical: Staking Ground in Dynamic Stabilization," In Vivo: The Business and Medicine Report, Windhover Information Inc., Mar. 2006, 10 pages.

Mathys Ltd., "Bone Cement—Product range", retrieved from: http://www.mathysmedical.com/index.php?id=70&type=98&L=1, accessed on Aug. 14, 2006, 2 pages.

Ostim®, retrieved from: http://www.aap.de/en/Produkte/Orthobiologie/Knochenersatz/Ostim, accessed on Aug. 14, 2006, 2 pages.

Parallax Medical, "Bone Cement", retrieved from: http://www.parallax-medical.com/index.php?pageId=33, accessed on Aug. 14, 2006, 17 pages.

Cardinal Health, "Special Procedures: Ava-Tex Bone Cement Delivery System", retrieved from: http://www.cardinal.com/mps/brands/specialprocedures/atsystem.asp, accessed on Aug. 14, 2006, 3 pages.

Zucherman, James F. et al., "A Multicenter, Prospective, Randomized Trial Evaluating the X STOP Interspinous Process Decompression System for the Treatment of Neurogenic Intermittent Claudication", Spine, 2005, pp. 1354-1358, vol. 30, No. 12.

Stryker, "Interventional Pain", retrieved from: http://www.stryker.com, accessed on Aug. 14, 2006, 6 pages.

Topoleski, L.D., et al., "The Fracture Toughness of Titanium-Fiber-Reinforced Bone Cement", Journal of Biomedical Materials Research, Abstract, Dec. 1992, vol. 26, No. 12.

Somatex® Cement, "Synthetic Bone Cement", 1 page.

Somatex® Medical Technologies GmbH, "Instructions for Use", CIS®, Cement Injection System, 4 pages.

Somatex® Medical Technologies GmgH, "Instructions for Use", Vertebroplasty-Canula, 10 pages.

Somatex® Medical Technologies GmgH, "Vertebroplasty: Treatment of Vertebral Compression Fractures", Pamphlet, 6 pages.

Somatex® Medical Technologies GmgH, "The Mixing System for Bone Cement", Pamphlet, 2004, 2 pages.

* cited by examiner

1

SYSTEMS AND METHODS FOR INJECTING BONE FILLER INTO THE SPINE

CLAIM OF PRIORITY

This application claims priority to U.S. Provisional Application No. 61/146,992, filed Jan. 23, 2009, entitled "Systems and Methods for Injecting Bone Filler into the Spine".

TECHNICAL FIELD

This present invention relates generally to spinal surgery, particularly systems and methods for injecting bone filler into the spine.

BACKGROUND

The human vertebral column (or "spine") connects the skull to the pelvis and includes a column of vertebrae, the sacrum, intervertebral discs and the coccyx. The vertebrae, which are the bones of the spine, function to bear the weight of the body and to house the spinal cord and spinal nerve roots within the vertebral column. There are two major parts to each vertebra: (1) the anterior (front) segment, which is the vertebral body; and (2) a posterior part (the vertebral arch) which encloses the vertebral foramen. The vertebral arch includes a pair of pedicles, a pair of laminae, and seven processes, four articular, two transverse and one spinous. The transverse processes are relatively long and slender while the spinous processes are relatively broad and thick. The processes provide sites for the attachment of ligaments and muscles which are important for the stability and movement of the spine.

Intervertebral discs lie between adjacent vertebrae in the spine. Each intervertebral disc includes a soft jelly-like center called the nucleus pulposus, which is surrounded by the annulus fibrosis, which includes several layers of fibrocartilage. The nucleus pulposus acts as a shock absorber for the spine, absorbing the impact of the body's daily activities and keeping the adjacent vertebrae separated. The nucleus pulposus is predominately made of water, which gives the intervertebral disc its elastic quality. However, as people age, the nucleus pulposus begins to dehydrate, which limits its ability to absorb shock and separate the adjacent vertebrae. This disc degeneration can result in spinal stenosis, a medical condition in which the spinal canal narrows, thereby producing pressure on the nerve roots resulting in pain and discomfort. Spinal stenosis can also be caused by spinal disc herniation, osteoporosis, or a tumor. Multiple different medical procedures have been developed to help alleviate the pain and discomfort associated with spinal stenosis.

One medical procedure that has been developed to alleviate the pain and discomfort associated with spinal stenosis includes distracting the spinous processes of adjacent vertebra using an interspinous implant. The interspinous implant can be placed between the spinous processes to increase the minimum distance between the spinous processes that occurs during extension motion, while substantially retaining flexion motion, axial rotation and lateral bending. The use of an interspinous implant may, however, place an unnatural amount of stress on the spinous processes supporting the interspinous implant. This can be problematic, especially when the spinous process has been weakened by old age and/or another medical condition (such as by osteoporosis). A weak spinous process may fracture or crack when using the implant. It can be desired to increase the strength of a spinous process, thereby allowing a wide range of interspinous implants to be used to distract the spinous processes of adjacent vertebra.

BRIEF DESCRIPTION OF THE DRAWINGS

Further details of the present invention are explained with the help of the attached drawings in which.

DETAILED DESCRIPTION

Figure 1A:
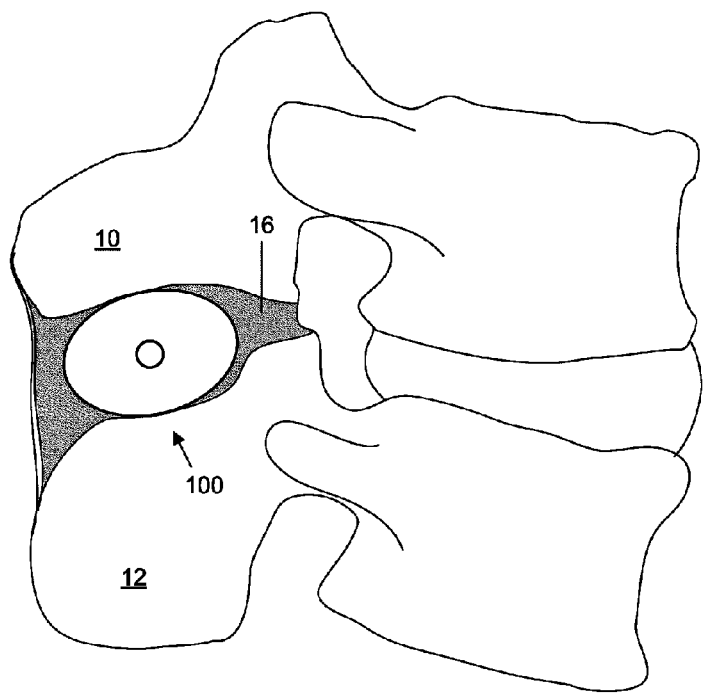
FIG. 1A is a side view of an extension limiting implant in accordance with the prior art positioned between adjacent spinous process.

Embodiments are described herein in the context of systems and methods for injecting bone filler (e.g., bone cement) into structures of the spine. One of ordinary skill in the art will appreciate that the following detailed description is illustrative only and is not intended to be in any way limiting. Other embodiments of the present invention will readily suggest themselves to one of ordinary skill in the art having the benefit of this disclosure. The scope of the invention should be ascertained with reference to the claims. In the description of the invention that follows, like numerals or reference designators will be used to refer to like parts or elements throughout. In addition, the left-most digit of a reference number identifies the drawing in which the reference number first appears.

An object of the invention is to provide systems and methods to augment the strength of one or more spinous processes to prevent the one or more spinous processes from fracturing or cracking when an interspinous implant is used to distract the spinous processes of adjacent vertebra. Another object of the invention is to generally strengthen weakened spinous processes and to repair cracked, fractured or otherwise damaged spinous processes. Another object of the invention is to provide a minimally invasive method of injecting bone filler into a spinous process. Additional objects, advantages, and embodiments of the invention are set forth in part in the description which follows, and in part, will be obvious from this description or may be learned from the practice of the invention.

Interaction of Implants and Spinal Structures

Figure 1B:
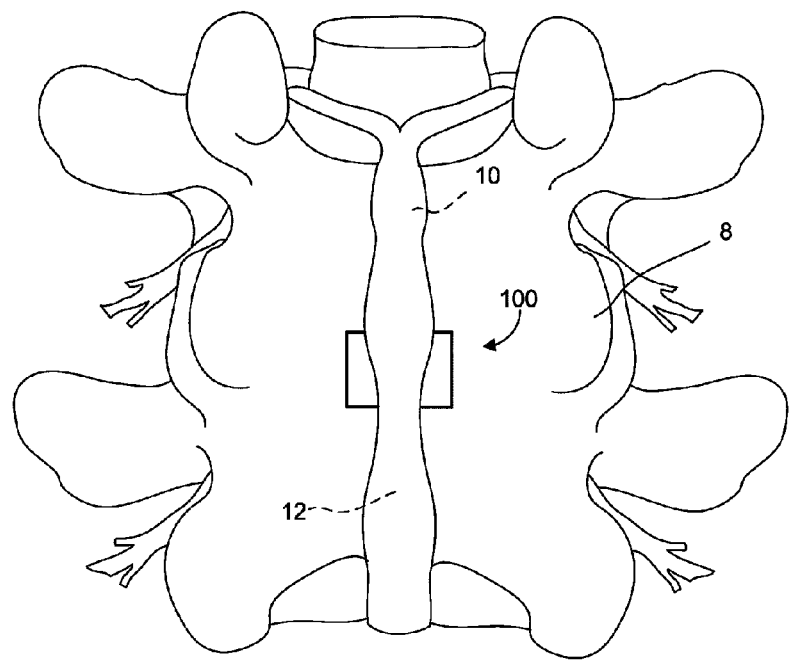
FIG. 1B is a posterior view of the extension limiting implant of FIG. 1A.

One medical procedure that has been developed to alleviate the pain and discomfort associated with spinal stenosis includes distracting the spinous processes of adjacent vertebra using an interspinous implant. The interspinous implant can be placed between the spinous processes to increase the minimum distance between the spinous processes that occurs during extension motion, while substantially retaining flexion motion, axial rotation and lateral bending. FIG. 1A is a side view and FIG. 1B is a posterior view of an interspinous implant 100 in accordance with the prior art positioned between adjacent spinous processes 10,12 to limit extension motion of the motion segment. The interspinous implant 100 comprises a spacer positioned between the adjacent spinous processes 10,12. The spacer limits extension motion by blocking relative movement of the adjacent spinous processes 10,12 that can cause the foraminal space to become undesirably small. The spacer floats between spinous processes 10,12, partially supported by the interspinous ligament 16 during flexion motion. Increasing the minimum foraminal space can relieve pressure on nerves caused by spinal stenosis and consequently reduce the pain caused thereby.

One example of an interspinous implant for limiting extension motion in accordance with the prior art is described in U S Pat. 6,699,246 to Zucherman et al. entitled, "Spine Distraction Implant." Other devices exist that restrict movement between spinous processes alone or in conjunction with devices for other treatments (e.g. spinal fusion cages). Such devices can rely on interaction with one or both of adjacent spinous processes for their operation and may place an unnatural amount of stress on the spinous processes. This can be problematic, especially when the spinous processes have degenerated or weakened due to old age and/or a medical condition (such as by osteoporosis). A weak spinous process may fracture or crack as stress is applied to the spinous process by an implant. It can therefore be desirable to increase the strength of the spinous process to allow a wide range of interspinous implants to be used in applications that restrict at least extension motion at a motion segment.

It would be desirable to enable a procedure for enhancing the strength of a spinous process of a patient. It would also be desirable to enable a minimally-invasive procedure for enhancing the strength of a spinous process of a patient. It would further be desirable to enable a procedure for enhancing the strength of a spinous process of a patient that could be performed in conjunction with a surgical intervention that affects the spinous process. It would still further be desirable to provide tools and instruments to facilitate a procedure for enhancing the strength of a spinous process of a patient.

Reinforcement of Spinous Processes

Generally, a spinous process and/or lamina can by strengthened by injecting a bone-filler material, such as polymethylmethacrylate (PMMA—commonly known as bone cement), into the spinous process and/or lamina. To accomplish this task, a bone filler injection device having bone filler can be inserted directly into a spinous process and/or lamina. The bone filler injection device may include a cannula which can be used to penetrate the bone and deploy the bone filler. Once the bone filler injection device is placed at the desired location within the bone, the bone filler can be injected. After the desired amount of bone filler has been injected, the bone filler injection device can be removed from the bone as the bone filler is allowed to cure.

Figure 2A:
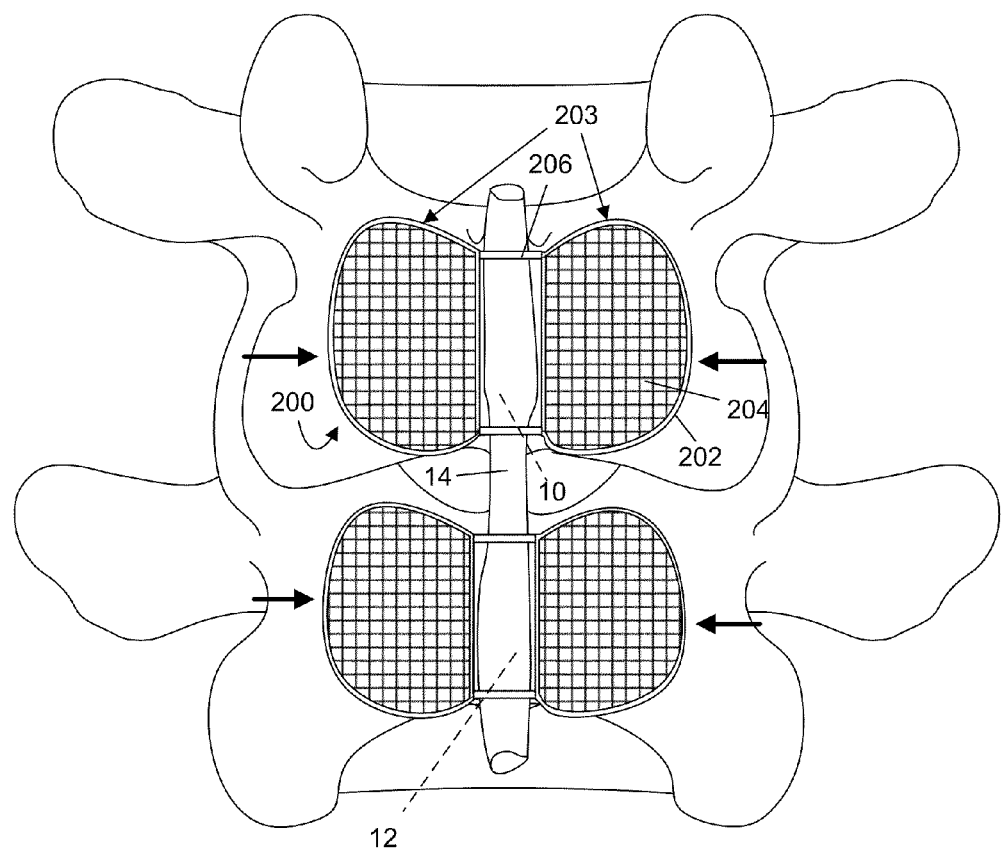
FIG. 2A is a posterior view of a framework arranged in a pre-deployed positioned, the framework usable with an embodiment of a system and method to reinforce a spinous process in accordance with the present invention.
Figure 2B:
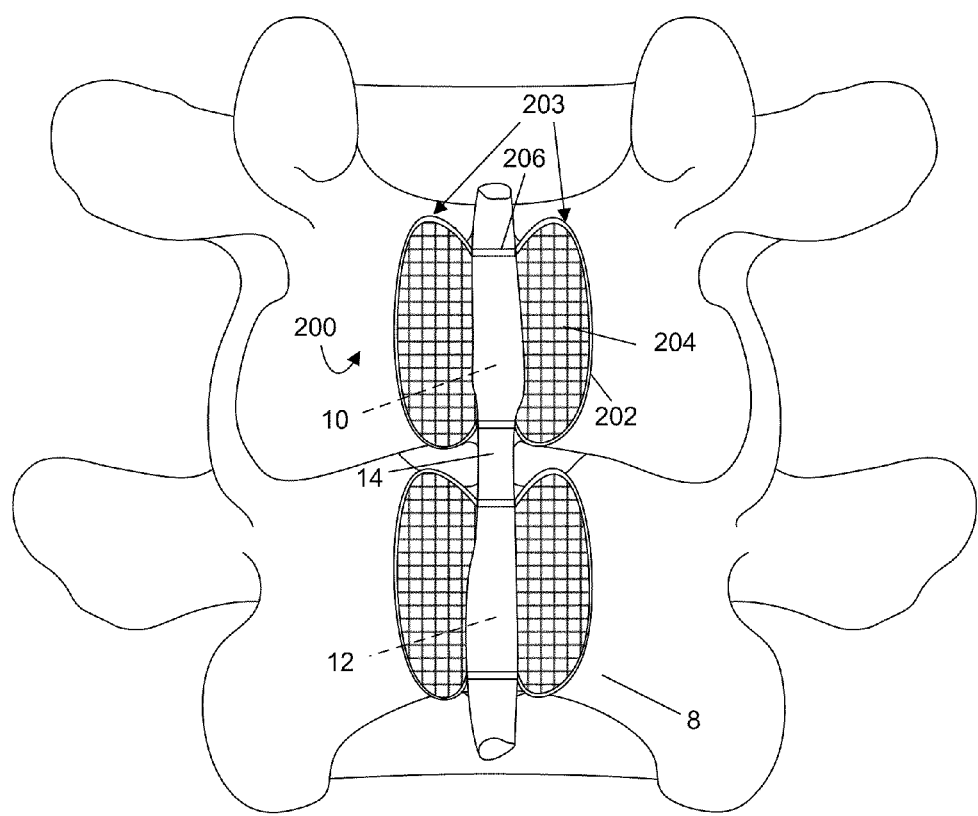
FIG. 2B is a posterior view of the framework of FIG. 2A arranged in a deployed position along the sides of adjacent spinous processes.
Figure 2C:
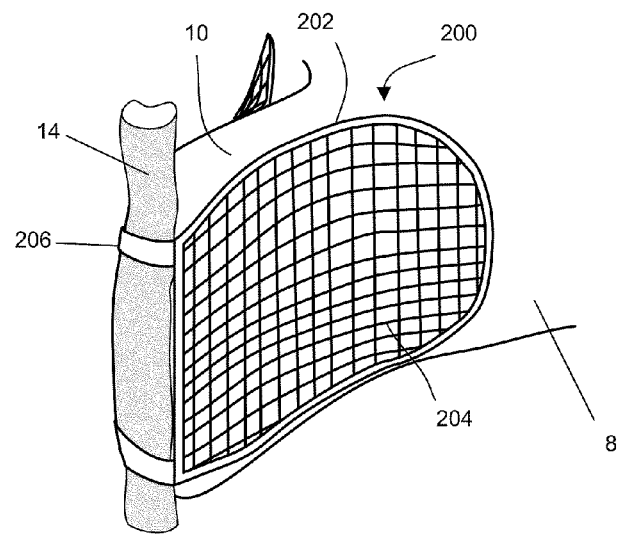
FIG. 2C is a perspective view of the framework of FIGS. 2A and 2B arranged in a deployed position sheathing a portion of a spinous process.

FIGS. 2A-2E illustrate an embodiment of a system and method of reinforcing one or more spinous processes in accordance with the present invention. FIG. 2A is a posterior view of a framework 200 positioned for implantation. The framework 200 comprises a pair of supports 203 each including a mesh 204 bounded by a frame 202. Preferably the supports 203 are connected to simplify implantation and improve predictability of placement of each support along the spinous process. The pair of supports 203 can be connected by a connecting structure comprising a bendable posts 206, flexible tape, or any structure that fixedly secures the pair of supports 203 to each other without damaging or otherwise irritating the supraspinous ligament 14 over which the connecting structure 206 is placed. The framework 200 should be fabricated from a biocompatible material that allows the framework 200 to flex so as to generally (though not necessarily perfectly) conform to the outer contours of the spinous process 10,12. The mesh should be sized so that the open spaces are sufficiently large to allow bone filler to enter the open spaces. Referring to FIG. 2B, the connecting structure can be bent or positioned over the supraspinous ligament 14 and the supports 203 can be urged into position so that the spinous process is substantially sheathed by the framework. Optionally, the reinforcement mesh 204 can extend along a portion of the lamina 8 connected with the spinous process. FIG. 2C is a perspective view showing the framework 200 positioned over the spinous process 10.

Figure 2D:
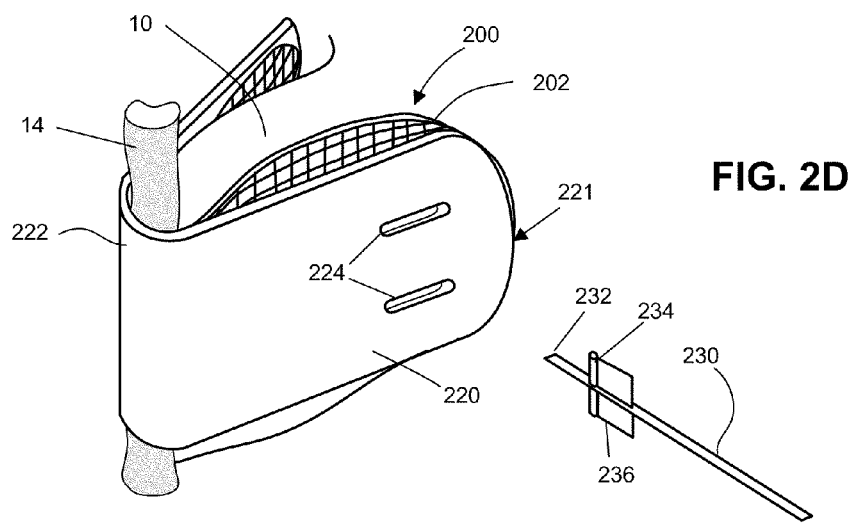
FIG. 2D is a perspective view of jig positioned over the framework with slots to receive a cannula and direct the cannula into a target spinous process.

Referring to FIG. 2D, a jig 220 can be positioned over the target spinous process 10 to guide a cannula (also referred to herein as an injection needle) 230 to one or more target locations (a pair of target locations as shown). The jig 220 can include one or more slots 224 to receive the cannula 230 in a desired orientation, for example like a keyholes. The cannula 230 can be shaped to complement the one or more slots, or alternatively the cannula 230 can include a stop 236 having a shape that complements a shape of the one or more slots 224, thereby causing the cannula 230 to assume a desired orientation to pass the stop 236 through the one or more slots 224. As shown, the jig 220 substantially sheaths the spinous process 10 and is aligned by urging a brace 222 of the jig 220 against the supraspinous ligament 14. Optionally, the jig 220 can be shaped to contact structures of the spine so that the jig 220 is generally directed into an appropriate position to guide the cannula 230 to the one or more target locations. For example, the jig 220 can have an anterior edge 221 that has a shape that follows the curve of the lamina. Thus, for a target spinous process of the lumbar region, the anterior edge 221 may curve in an anterior direction from the inferior articular process (i.e., the inferior facet) toward the superior articular process (i.e., the superior facet), as goes the general curve of the lamina structure. In general, a jig 220 for use in embodiments of systems and methods in accordance with the present invention should be sized and shaped so as to align relative to the target spinous process to enable a user to guide a cannula 230 to one or more target locations with reasonable accuracy and precision. A jig need not necessarily sheath the spinous process. For example, a jig supported by the lamina need not include a brace and can contact a single side of the spinous process.

Figure 7A:
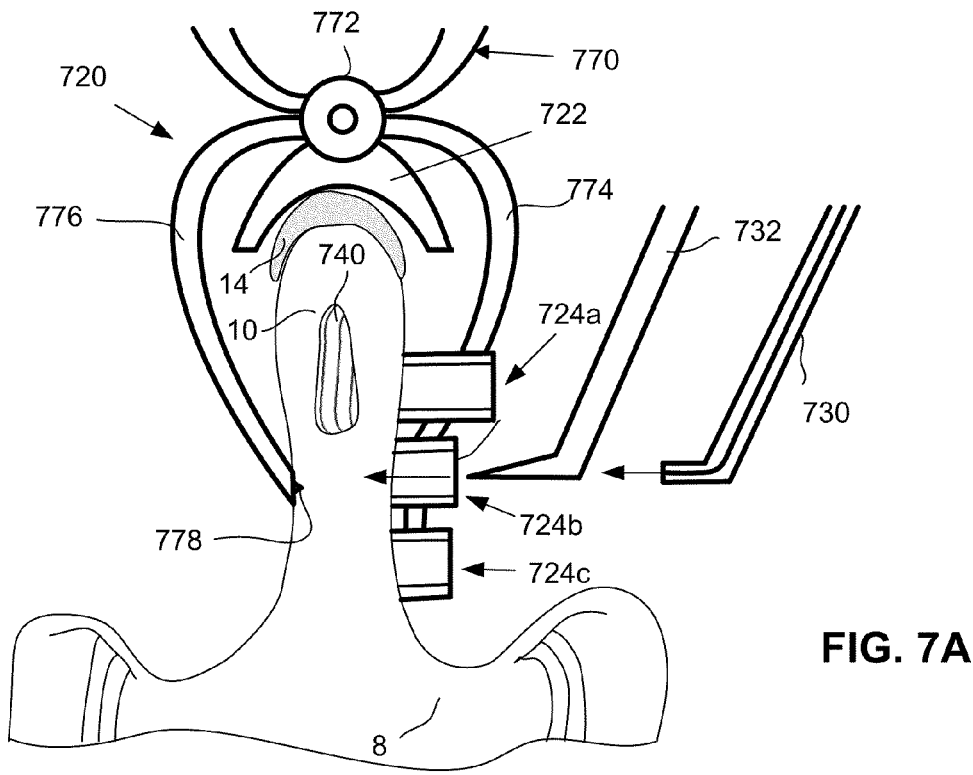
FIG. 7A is a superior view of a jig usable with a still further embodiment of a system and method positioned over a target spinous process.
Figure 9A:
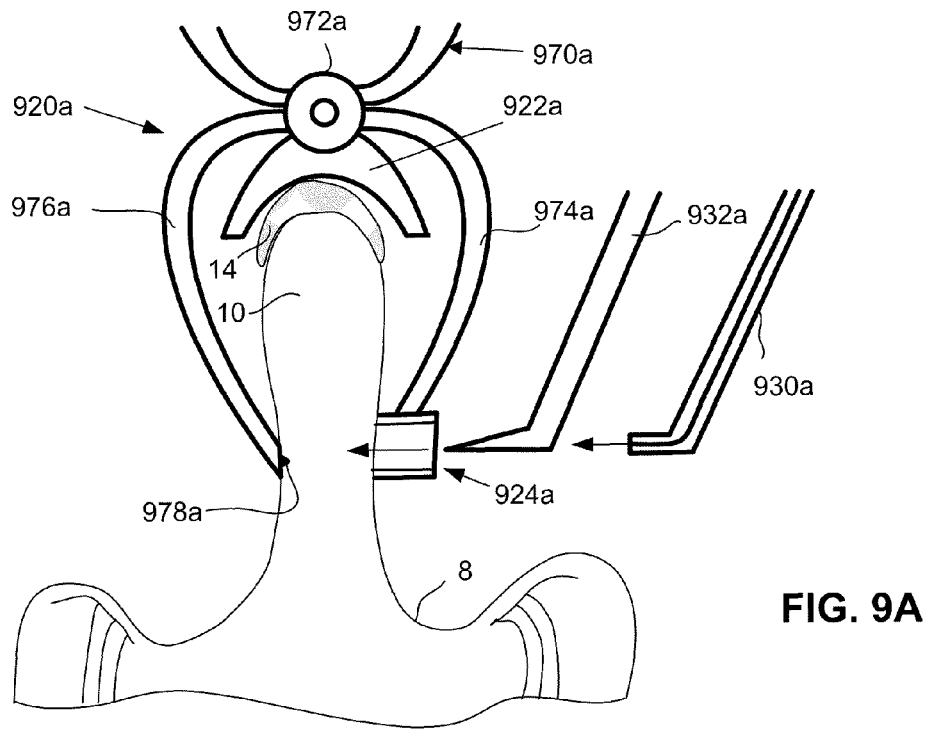
FIG. 9A is a superior view of a first jig of a series of jigs usable with another embodiment of a system and method positioned over a target spinous process.

The insertion of a cannula 230 into the spinous process 10 and/or lamina 8 may be accomplished using different techniques. In an embodiment, the cannula 230 includes a bevelled distal end 232 which can be pushed and/or driven into the spinous process 10 and/or lamina 8. In another embodiment, a two-step technique may be used to introduce the bone filler into the spinous process 10 and/or lamina 8. In such embodiments, a drill and/or point (e.g., an awl, as shown in FIGS. 7A and 9A) can be used to enter the cortex of the spinous process 10 and/or lamina 8 to create an initial path to the desired treatment site. Once a path has been created, the drill and/or point is removed and the cannula is inserted into the path within the spinous process 10 and/or lamina 8. For a two-step technique, the cannula may include a blunt distal end to prevent the cannula from extending past the endpoint of the path. This helps to ensure that the bone filler remains inside the spinous process 10 and/or lamina 8. Optionally, a diameter of the path can be slightly smaller than the diameter of the cannula to prevent the filler from flowing back out of the path that was created. Accordingly, the path could be narrow enough to require the user to apply a force to the cannula in order to insert it into the path, but wide enough to reduce amount of force which is needed to do so. Once inserted, the cannula should fit snugly within the path.

Turning now specifically to the cannula 230, the cannula 230 can be any commercially available cannulated needle as envisioned by one having an ordinary skill in the art having the benefit of this disclosure. The cannula 230 is preferably non-reactive, made of medical grade material and includes a stylet to prevent filler and/or bond blockage. The diameter of the cannula 230 should be small enough to minimize injury to the body and yet large enough to permit the bone filler 240 to flow into the spinous process 10 and/or lamina 8. In an embodiment, an eleven to fourteen gauge cannula can be used. It is, however, envisioned that smaller and/or larger needle diameters can also be used without deviating from the scope of the invention.

Figure 2E:
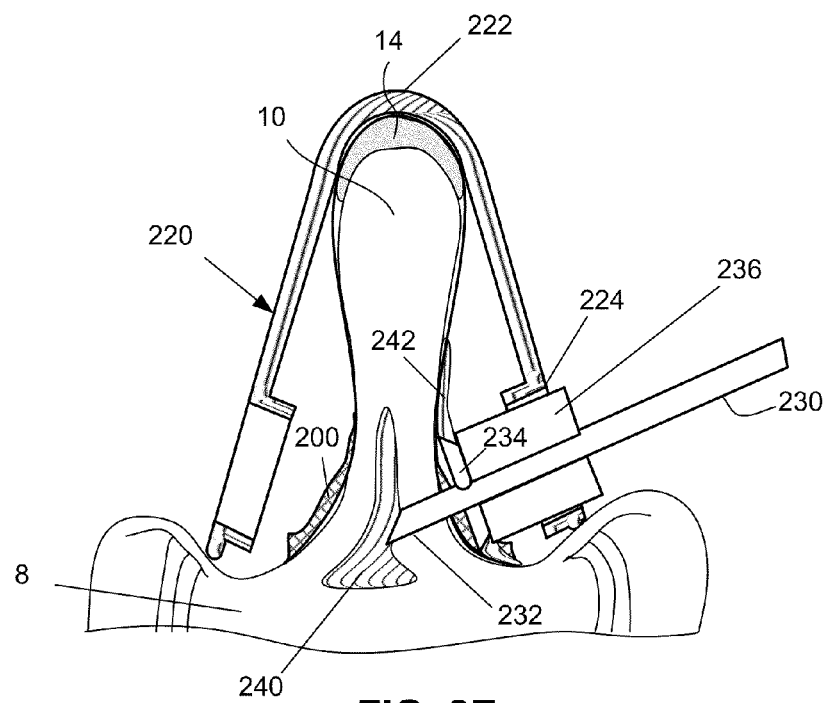
FIG. 2E is a superior view of the arrangement illustrated in FIG. 2D, with the cannula penetrating the spinous process.

FIG. 2E is a superior view showing a partial cross-section of a jig 220 and spinous process 10 and illustrating the cannula 230 positioned at a target location. The cannula 230 further includes side delivery tubes 234 (as shown in 2D and 2E) or apertures to deposit bone filler 242 over the framework 200 and the outer surface of the spinous process 10 so that bone filler 242 coats and contacts or penetrates the mesh 204 to provide a supporting shell for the spinous process. The bone filler 242 can fill voids in the spinous process 10 and area between the mesh and the outer surface of the spinous process 10 to mate the framework 200 with the spinous process 10. As shown, the jig 220 guides the cannula 230 into proper alignment. The delivery tubes 234 can be sized and shaped to act as a depth gauge, limiting the depth to which the cannula 230 penetrates into the spinous process 10. When the cannula 230 reaches a proper depth, bone filler 240 is injected at the target location, preferably filling cracks and voids and reinforcing the spinous process 10. Once injection is complete, the cannula 230 can be removed and the process can be repeated at another of the one or more slots 224 of the jig 220. Once the bone filler injection is complete, the jig 220 can be removed from spinous process 10, and the bone filler 240,242 can be permitted to cure. Optionally, the bone filler material 242 coating the framework 200 and outer surface of the spinous process 10 can be supplemented or redistributed to ensure acceptable coverage and reduce excess material that can become an irritant to tissues. While the injection of bone filler at a target location is described separate from deposition of bone filler 242 over the framework 200, as shown in FIG. 2E, bone filler 240,242 can be provided to both locations simultaneously, or alternatively sequentially in either order.

Figure 2F:
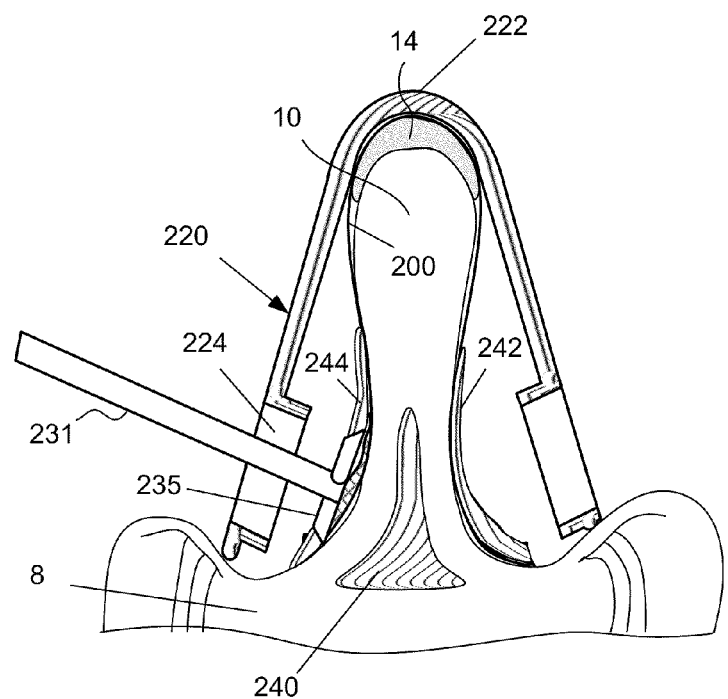
FIG. 2F is a superior view of the arrangement illustrated in FIGS. 2D and 2E, with a supplemental cannula dispensing bone filler over an outer surface of the spinous process.

FIG. 2F illustrating a supplemental cannula 231 positioned to deposit bone filler 244 to an outer surface at an opposite side of the target spinous process 10. The supplemental cannula 231 need not penetrate the spinous process 10 and can include myriad different shapes and configurations for dispensing bone filler in a generally predictable manner such that the bone filler coats and contacts or penetrates the mesh of the framework 200 to provide a supporting shell for the spinous process. The bone filler 244 can fill voids in the spinous process 10 and areas between the mesh and the outer surface of the spinous process 10 to mate the framework 200 with the spinous process 10. As shown, the supplemental cannula 231 includes a blunt, sealed distal end with a pair of deliver tubes 235 extending perpendicular to the shaft of the supplemental cannula 231. It should be noted that the bone of the spinous process 10 may be porous enough such that in some embodiments in accordance with the present invention injection of a sufficient volume of bone filler 240 into the spinous process 10 may result in bone filler 240 oozing or otherwise penetrating to the outer surface of the spinous process and contacting the mesh of the framework 200, supplanting a need for coating the mesh with bone filler 242 by way of delivery tubes arranged adjacent the outer surface of the spinous process 10.

Optionally, the one or more slots of the jig may vary in shape and correspond to specific needles from a cannula set. In such embodiments, the system can comprise a kit of a jig and multiple cannulas. Multiple cannulas can have differing depths of penetration, for example. The one or more slots of the jig can vary in number and position along the jig, for example so that locations can be targeted along the spinous process from the lamina in a posterior direction toward the supraspinous ligament.

Figure 3A:
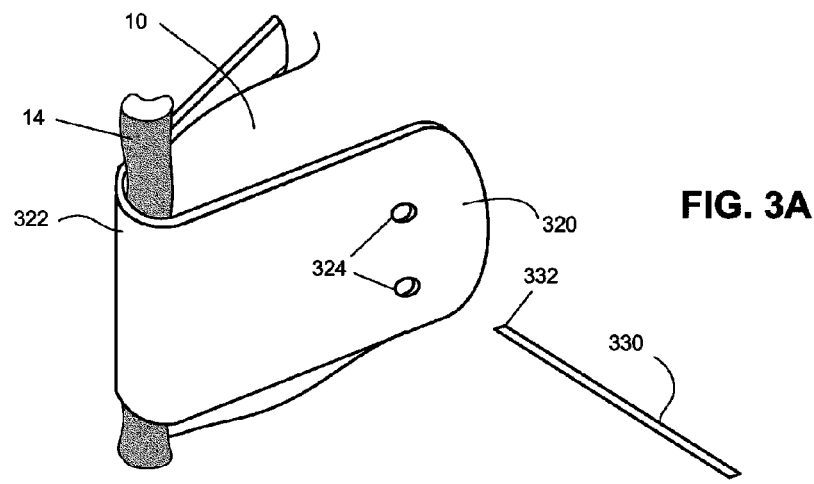
FIG. 3A is a perspective view of a jig usable with an alternative embodiment of a system and method in accordance with the present invention, the jig positioned over the spinous process and having slots to receive a cannula and direct the cannula into a target spinous process.

FIGS. 3A-3D illustrate an alternative embodiment of a system and method of reinforcing one or more spinous processes in accordance with the present invention. FIG. 3A is a perspective view of a jig 320 positioned over the target spinous process 10 to guide a cannula 330 to one or both of two target locations. The jig 320 includes two slots 324 to receive the cannula 330. As shown, the jig 320 substantially sheaths the spinous process 10 and is aligned by urging a brace 322 of the jig 320 against the supraspinous ligament 14. As above, optionally the jig 320 can be shaped to contact structures of the spine so that the jig 320 is generally directed into an appropriate position to guide the cannula 330 to the one or more target locations.

Figure 3B:
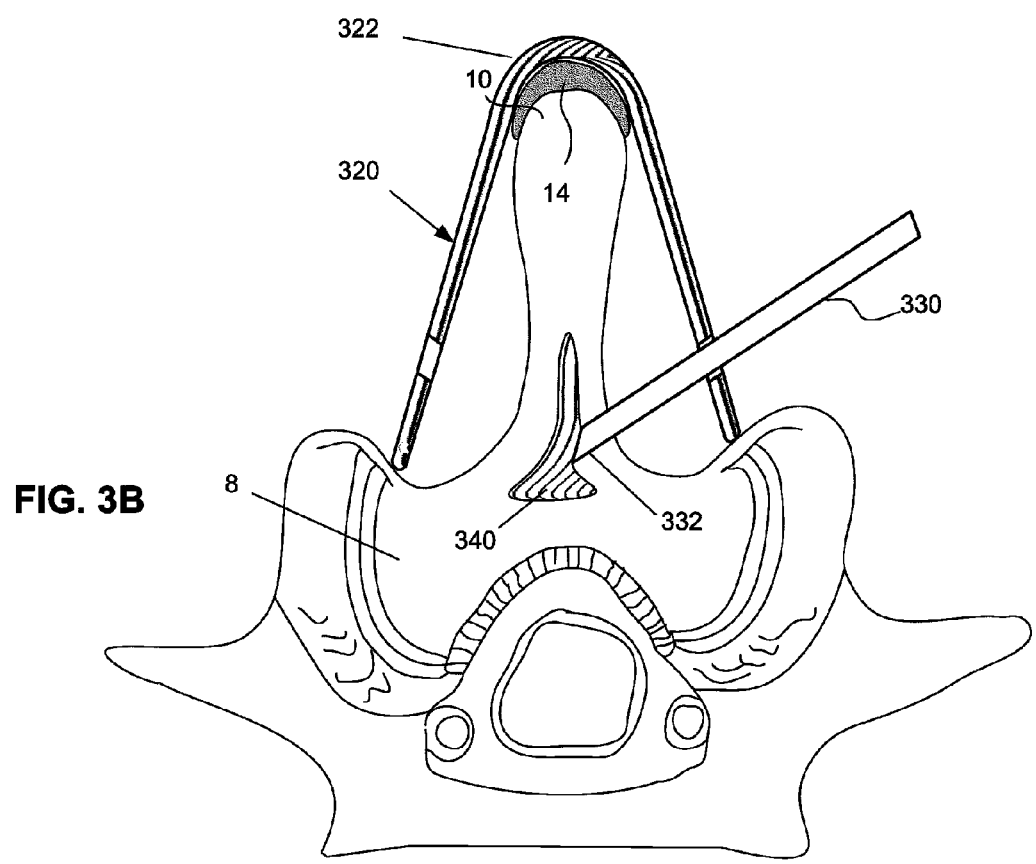
FIG. 3B is a superior view of the arrangement illustrated in FIG. 3A, with the cannula penetrating the spinous process.

As shown in FIGS. 3A and 3B the slots 324 and cannula 330 have a round shape that allows the cannula 330 to rotate about an axis through the slots 324. If a distal end 332 of the cannula 330 is bevelled, a user may desire to take care as to the angle of entry of the bevel while urging the distal end 332 into the spinous process to improve the predictability of results when bone filler is urged into the spinous process. This can be accomplished, for example, by marking on one or both of the jig 320 and cannula 330 to provide a visual cue to the user as to the orientation of the bevel. Alternatively, the slots 324 can be shaped to accept in a desired orientation a cannula 330 having a complementary outer surface shape. For example, the slots 324 and cannula 330 can be ovoid in shape. Further, as shown the cannula 330 does not include a stop to limit depth of insertion. Optionally, the cannula 330 can be marked to enable determination of location of the proximal end 332. Alternatively, the cannula 330 can include a feature such as a stop, stop, and/or change in outer surface shape that restricts movement of the cannula 330 through the jig 320.

Figure 3C:
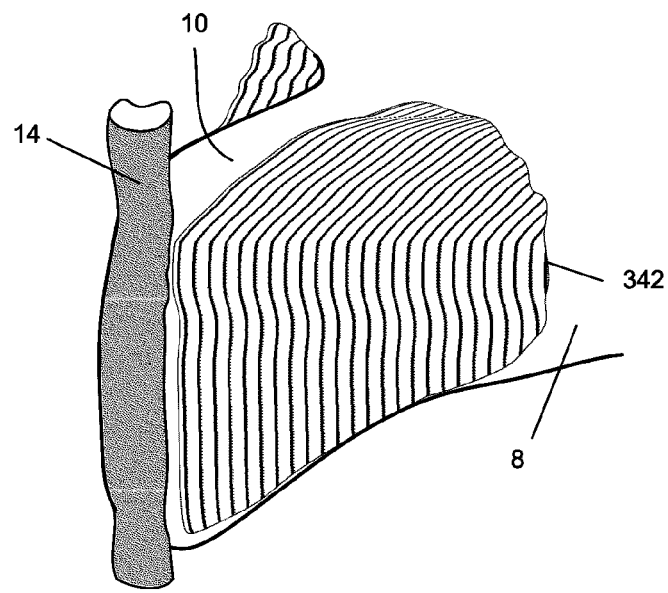
FIG. 3C is a perspective view of the spinous process of FIGS. 3A and 3B including bone filler applied along the sides of the spinous process.
Figure 3D:
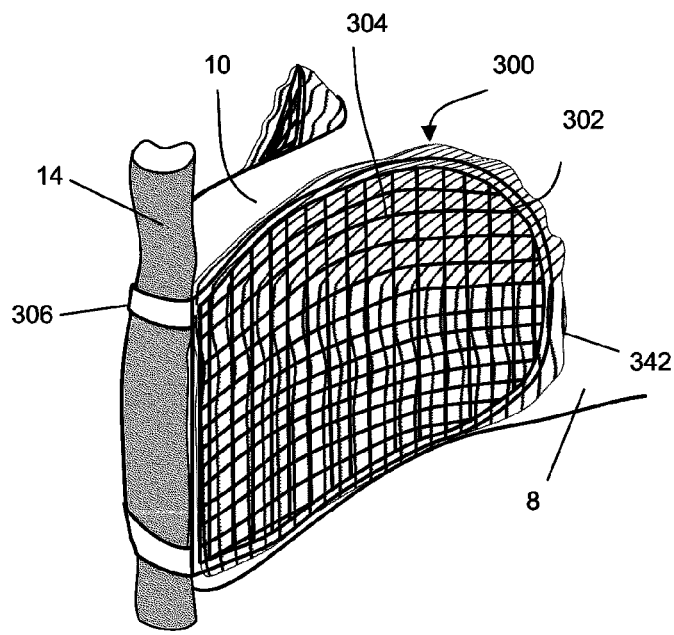
FIG. 3D is a perspective view of the spinous process of FIGS. 3A and 3B including a framework sheathing a portion of the spinous process and embedded in the bone filler.

Referring to the perspective views of FIGS. 3C and 3D, once the bone filler 340 has been satisfactorily injected into the spinous process, the jig 320 is removed and bone filler 342 is applied to the outer surface of the spinous process. A framework 300 can then be sheathed over the spinous process with connecting structures 306 simplifying the positioning of supports over the spinous process. The frame 302 and mesh 304 can be urged against the outer surface of the spinous process so that the bone filler 342 contacts and/or penetrates the mesh 304 so that the mesh 304 is embedded in the bone filler 342. The bone filler 342 can then be allowed to cure so that the framework 300 and bone filler 342 reinforce the spinous process.

Figure 4A:
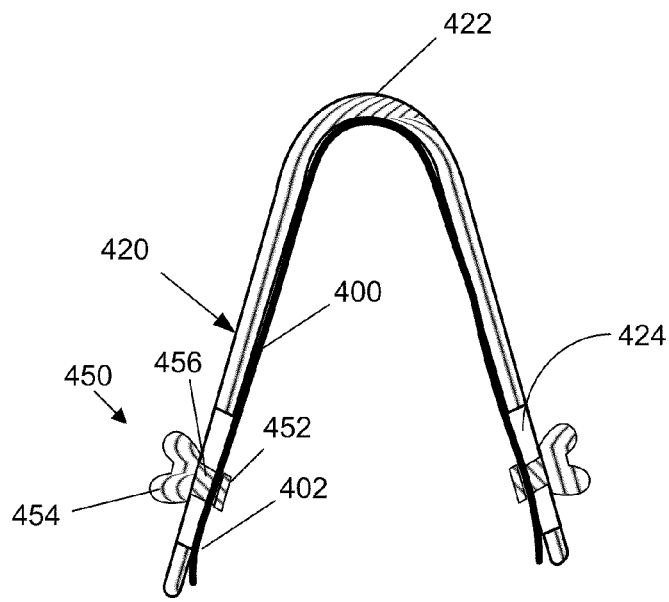
FIG. 4A is a superior view of a jig and framework comprising shape memory material coupled for positioning over a spinous process.
Figure 4B:
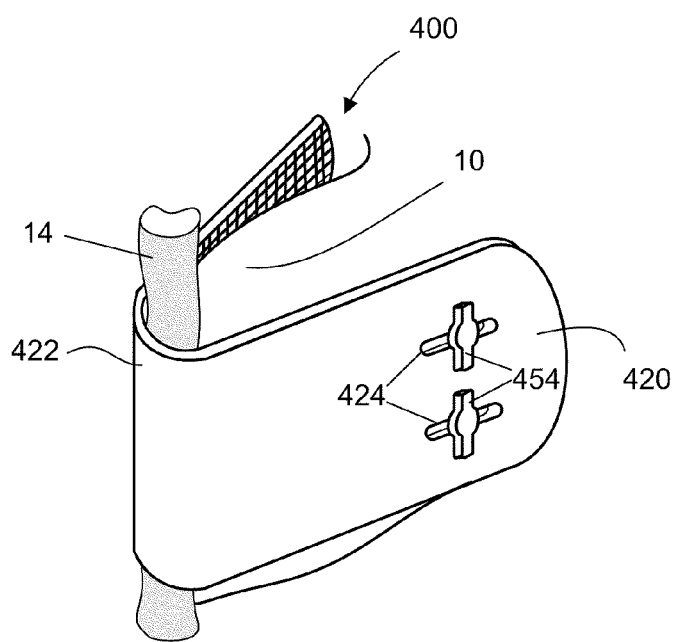
FIG. 4B is a superior view of the jig and framework of FIG. 4A with the framework decoupled from the jig so that the framework takes a preset shape.

FIGS. 4A-4G illustrate a further embodiment of a system and method of reinforcing one or more spinous processes in accordance with the present invention. FIG. 4A is a superior view of a jig 420 connected with a framework 400 comprising a frame 402 and mesh 404, one or both of which is fabricated from of a shape memory material. The framework 400 can be held close to the contours of the jig 420 by a plurality of retainers 450 positioned within corresponding slots 424 of the jig 420 to allow for preparatory positioning of the framework 400 over a target spinous process 10 (as shown in the perspective view of FIG. 4B). A retainer 450 can comprise a block 452 connected to a knob 454 by a stem 456, the block having a shape, for example, that complements a corresponding slot 424 so that when the retainer 450 is rotated the block 452 cannot pass through the slot 424.

Figure 4C:
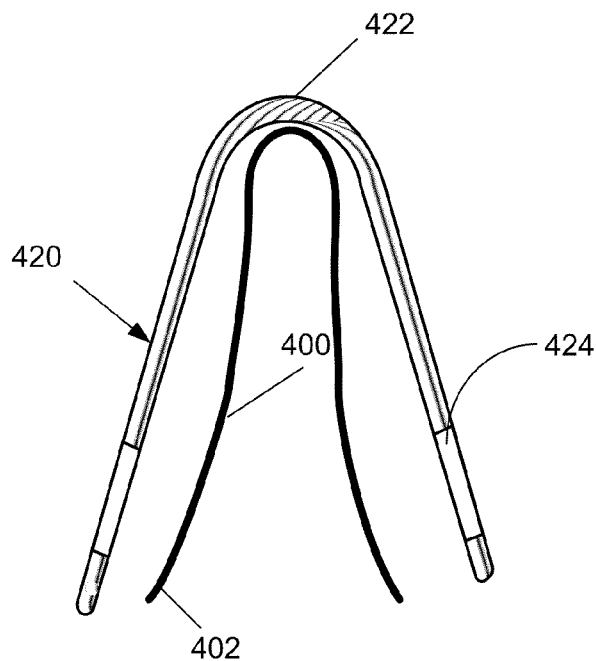
FIG. 4C is a perspective view of the jig and framework coupled as shown in FIG. 4A and positioned over a target spinous process.
Figure 4D:
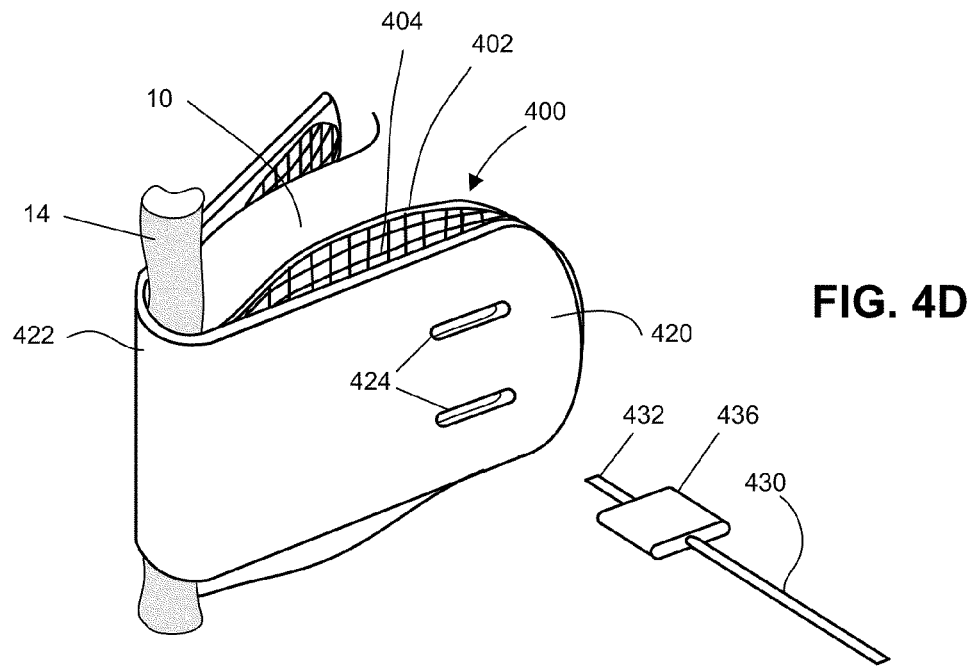
FIG. 4D is a perspective view of the jig and framework decoupled so that the framework takes a shape substantially conformal with the outer surface of the target spinous process.

Referring to FIGS. 4C and 4D, once positioned over the target spinous process, the plurality of retainers 450 can be removed, thereby permitting the framework 400 to assume a shape that generally sheaths the spinous process. The slots 424, now unobstructed, guide a cannula 430 to one or both of two target locations. The jig 420 includes two slots 424 to receive the cannula 430, although in other embodiments the jig 420 can include additional slots 424. The jig 420 substantially sheaths the spinous process 10 and is aligned by urging a brace 422 of the jig 420 against the supraspinous ligament 14. As above, optionally the jig 420 can be shaped to contact structures of the spine so that the jig 420 is generally directed into an appropriate position to guide the cannula 430 to the one or more target locations.

Figure 4E:
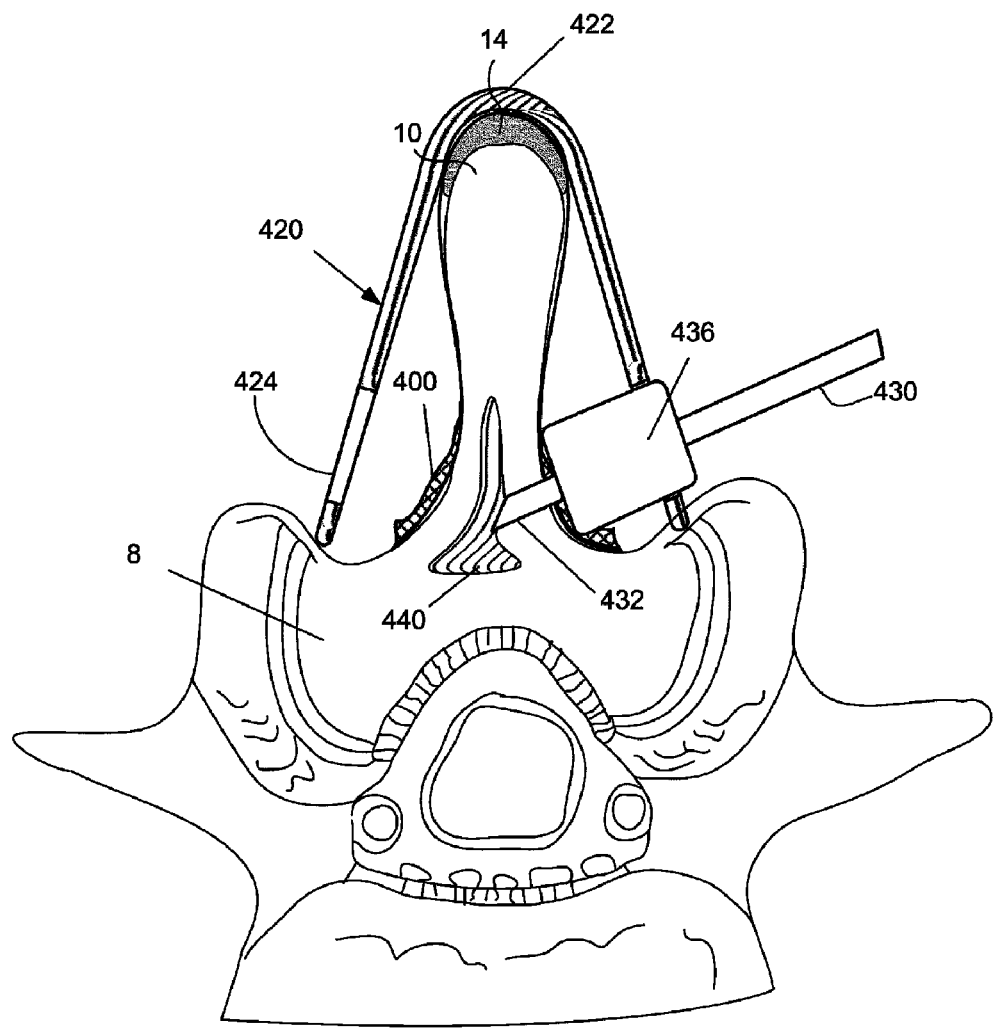
FIG. 4E is a superior view of the arrangement illustrated in FIG. 4D, with a cannula penetrating the spinous process.

As shown in FIG. 4D, the cannula 430 can include a stop 436 having a shape that matches a shape of the one or more slots 424, thereby causing the cannula 430 to assume a desired orientation to pass through the one or more slots 424. If a distal end 432 of the cannula 430 is bevelled, the complementary shapes of the slot 424 and the cannula 430 can ensure the angle of entry of the bevel while urging the distal end 432 into the spinous process to improve the predictability of results when bone filler is urged into the spinous process. FIG. 4E is a superior view showing a partial cross-section of the jig 420 and spinous process 10 and illustrating the cannula 430 positioned at a target location. The stop 436 can be sized and shaped to act as a depth gauge, limiting the depth to which the cannula 430 penetrates into the spinous process 10. When the cannula 430 reaches a proper depth, bone filler 440 is injected at the target location, preferably filling cracks and voids and reinforcing the spinous process. Once injection is complete, the cannula 430 can be removed and the process can be repeated at another of the one or more slots 424 of the jig 420. Optionally, the one or more slots 424 may vary in shape and correspond to specific needles from a cannula set. In such embodiments, the system can comprise a kit of a jig and multiple cannulas. Multiple cannulas can have differing depths of penetration, for example. The one or more slots of the jig can vary in number and position along the jig, for example so that locations can be targeted along the spinous process from the lamina in a posterior direction toward the supraspinous ligament.

Figure 4F:
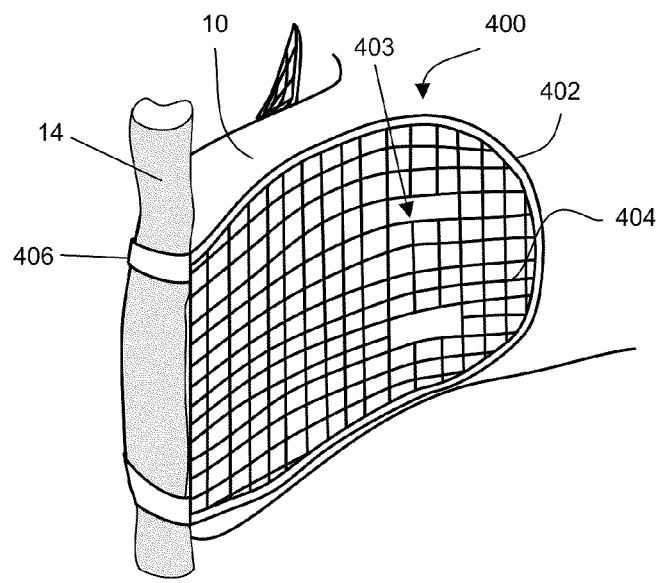
FIG. 4F is a perspective view of the framework of FIG. 4A-4E arranged in a deployed position sheathing a portion of a spinous process with the jig removed from around the framework.
Figure 4G:
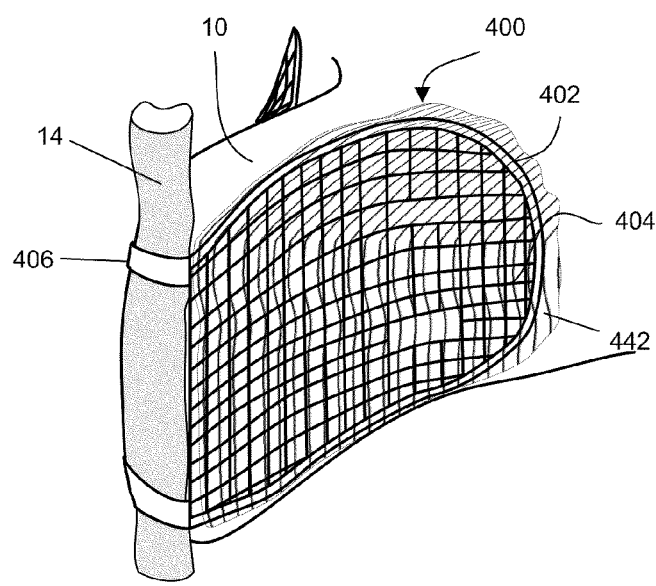
FIG. 4G is a perspective view of the framework arranged as shown in FIG. 4F and coated in bone filler.

Referring to the perspective views of FIGS. 4F and 4G, once the bone filler 440 has been satisfactorily injected into the spinous process, the jig 420 is removed and bone filler 442 can be applied to the outer surface of the spinous process over the framework 400 so that the bone filler 442 fills spaces within the mesh 404 of the framework 400 so that the mesh 404 is embedded in the bone filler 442. The bone filler 442 can then be allowed to cure so that the framework 400 and bone filler 442 reinforce the spinous process. As can be seen in FIGS. 4F and 4G, the mesh 404 can include gaps 403 to accommodate the block 452 of the retainer 450. While the embodiment of FIGS. 4E-4G shows application of bone filler 442 to the outer surface of the spinous process after removal of the jig 420, alternatively a cannula resembling the cannula 230 of FIG. 2E can be used to distribute bone filler over the outer surface of the spinous process simultaneously with the injection of bone filler into the spinous process.

Figure 5A:
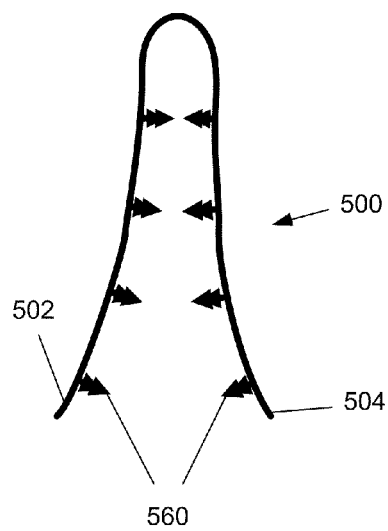
FIG. 5A is a superior view of a framework usable with an alternative embodiment of a system and method to reinforce a spinous process in accordance with the present invention.
Figure 5B:
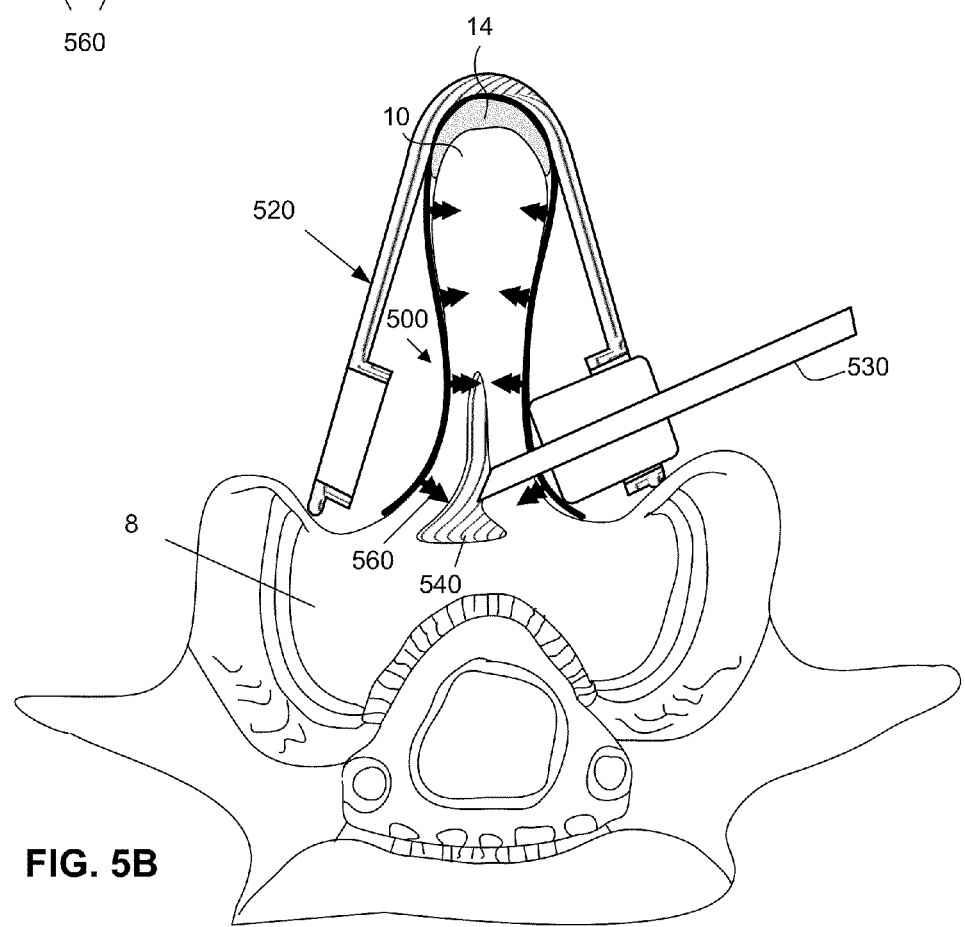
FIG. 5B is a superior view of a jig and the framework of FIG. 5A positioned over a target spinous process with a cannula penetrating the spinous process.

FIGS. 5A-5D illustrate a further embodiment of a system and method of reinforcing one or more spinous processes in accordance with the present invention. FIG. 5A is a superior view of a framework 500 for use with the embodiment and including a plurality of anchors 560 extending from one or both of a frame 502 and a mesh 504. The framework 500 can be fabricated from a flexible or semi-flexible material having sufficient stiffness and/or resilience to enable the anchors to be urged into the spinous process, for example by application of pressure to individual anchors by hand or a plurality of anchors by tool. Alternatively, the framework 500 can be fabricated from a shape memory material that assists a user to urge the anchors in position by causing the framework 500 to collapse around the spinous process. As shown in FIG. 5B, once the framework 500 is in position a jig 520 can be placed around the spinous process (as above) to guide a cannula 530 into position for injection of bone filler 540 into the body of the spinous process 10 and/or a portion of the lamina 8.

Figure 5C:
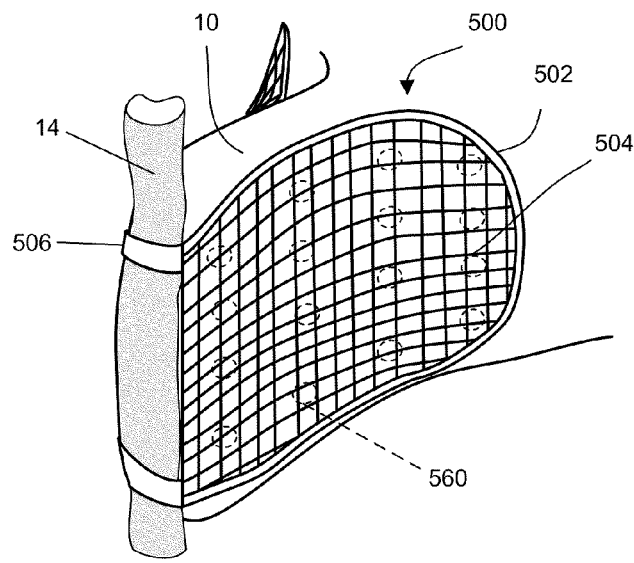
FIG. 5C is a perspective view of the framework of FIG. 5A sheathing a portion of the spinous process with the jig removed from around the framework.
Figure 5D:
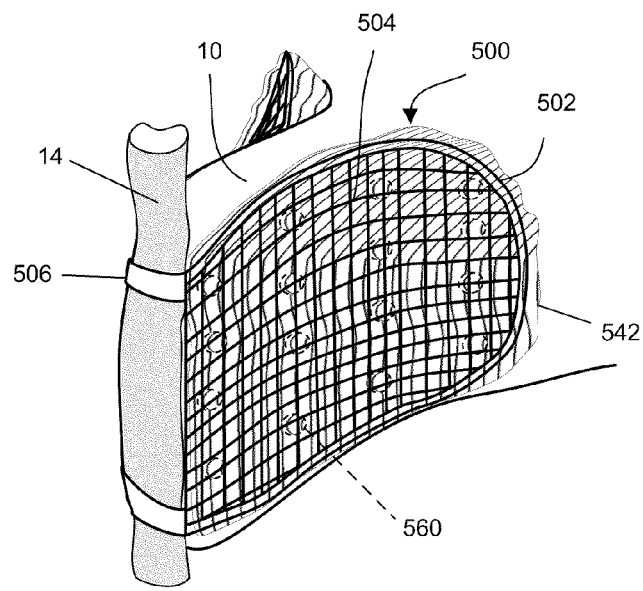
FIG. 5D is a perspective view of the framework arranged as shown in FIG. 5C and coated in bone filler.

Referring to the perspective views of FIGS. 5C and 5D, a grid of anchors is shown implanted in the spinous process 10. After the jig 520 has been removed, bone filler 542 can be applied to the outer surface of the spinous process 10 so that the bone filler 542 contacts and/or penetrates the mesh 504 of the framework 500 to form a substantially integral structure supporting the spinous process 10. While the embodiment of FIGS. 5B-5D shows application of bone filler 542 to the outer surface of the spinous process 10 after removal of the jig 520, alternatively a cannula resembling the cannula 230 of FIG. 2E can be used to distribute bone filler over the outer surface of the spinous process simultaneously with the injection of bone filler into the spinous process.

Figure 6A:
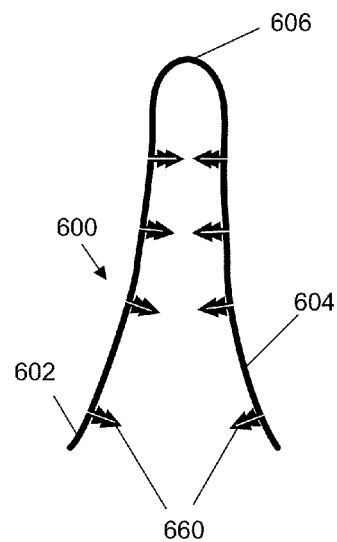
FIG. 6A is a superior view of a framework usable with a further embodiment of a system and method to reinforce a spinous process in accordance with the present invention.
Figure 6B:
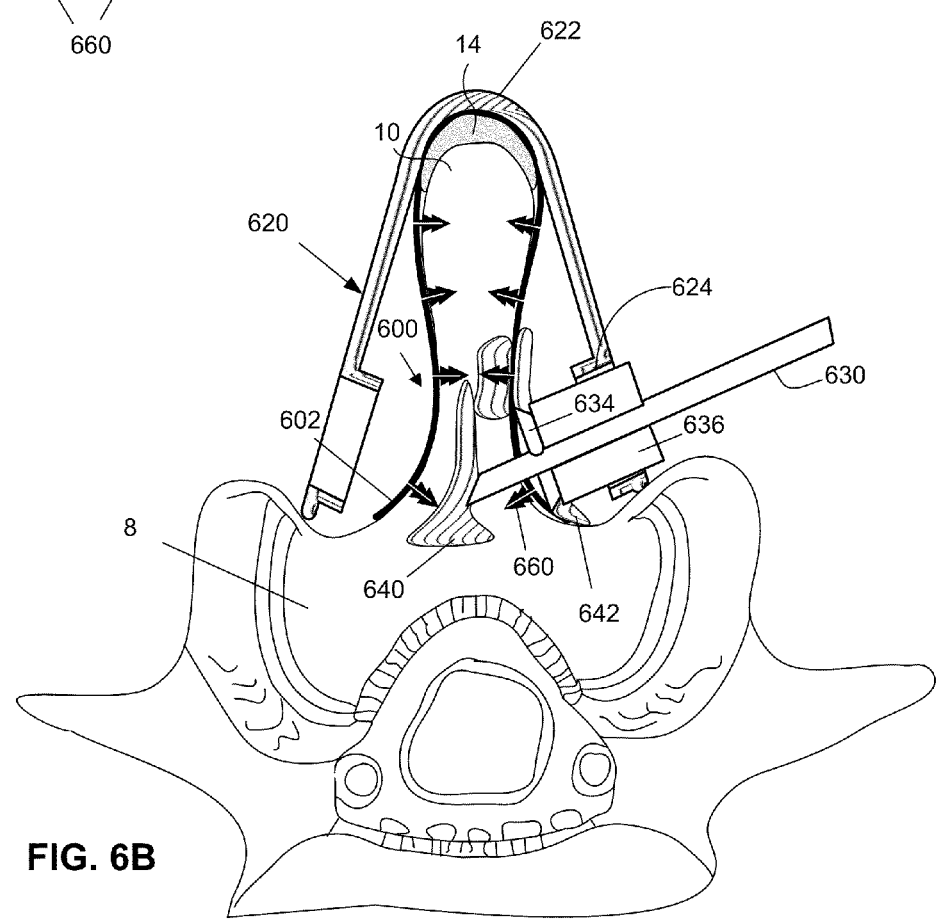
FIG. 6B is a superior view of a jig and the framework of FIG. 6A positioned over a target spinous process with a cannula penetrating the spinous process.

FIGS. 6A and 6B illustrate a further embodiment of a system and method of reinforcing one or more spinous processes in accordance with the present invention resembling the previous embodiments. FIG. 6A is a superior view of a framework 600 for use with the embodiment and including a plurality of anchors 660 extending from one or both of a frame 602 and a mesh 604, as above. However, the anchors can comprise a porous structure sufficiently capable of passing bone filler with a sufficiently low viscosity. For example, bone cements are provided as two-component materials consisting of a powder (i.e., pre-polymerized PMMA and/or PMMA or MMA co-polymer beads and/or amorphous powder) and a liquid (i.e., MMA monomer). The two components are mixed and a free radical polymerization occurs. Bone cement viscosity changes over time from a runny liquid into a dough-like state that can be safely applied and then finally hardens into solid hardened material. As shown in FIG. 6B, a jig 620 can be positioned over the spinous process, and a cannula 630 including a stop 636 and side deliver tubes 634 can be inserted into slots 624 of the jig 620 to deliver bone filler 640,642 to the body of the spinous process 10 and/or a portion of the lamina 8, and to an outer surface of the spinous process 10 and/or lamina 8. Preferably, a low viscosity bone filler seeps into the spinous process by way of one or more anchors 660.

FIGS. 7A-7D illustrate a further embodiment of a system and method of reinforcing one or more spinous processes in accordance with the present invention comprising one or more clamping tools for guiding piercing and/or filling tools. FIG. 7A is a superior view of a guide clamp 720 comprising a brace 722 that is urged against the supraspinous ligament 14 and connected with a pivot 772. A first arm 776 is clamped in position (by way of the handle 770) on one side of a target spinous process 10 with a spike 778 for resisting slippage while a second arm 774 closes over and against an opposite side of the spinous process 10 with slots 724a-724c of variable or similar size providing a template for an awl 732 and cannula 730, or a series of awls and cannulas corresponding to the different slots 724a-724c. Alternatively, the cannula 730 can include a bevelled distal end capable of piercing the bone as well as depositing bone filler 740. A series of bone filler injections can be performed at the slots 724a-724c to reinforce the body of the spinous process 10. Once the injections are complete, the guide clamp 720 can be released and removed from the spinous process 10.

Figure 7B:
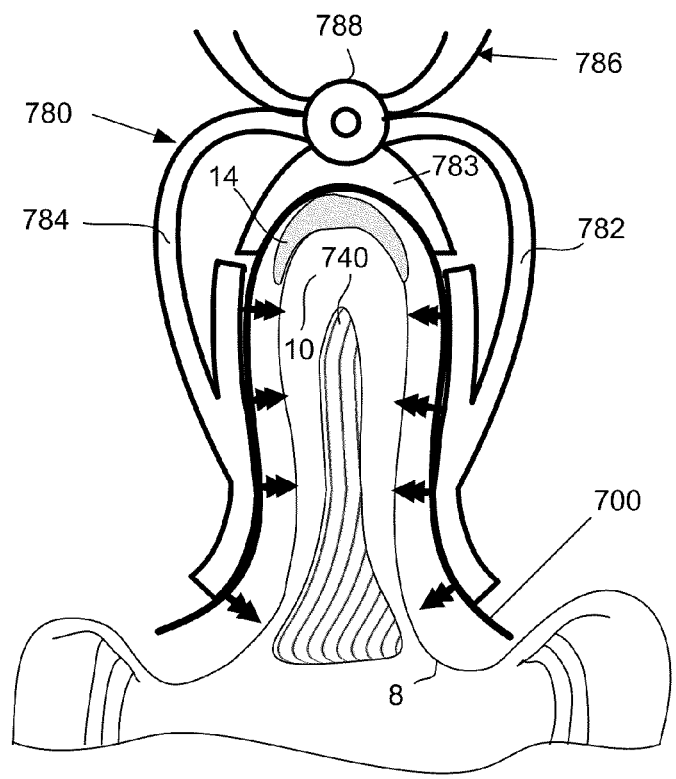
FIG. 7B is a superior view of a pliers usable to position a framework usable with the still further embodiment of the system and method of FIG. 7A.
Figure 7C:
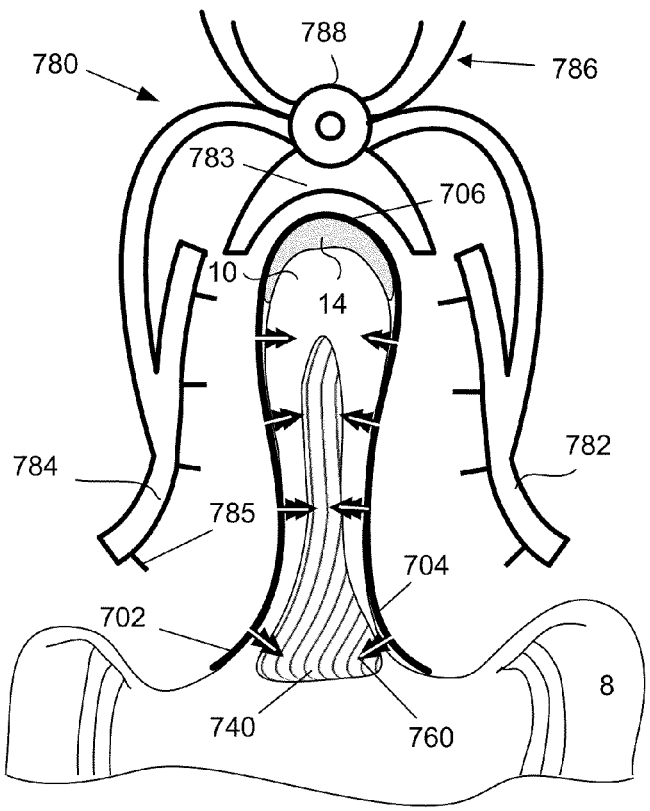
FIG. 7C is a superior view of the pliers of FIG. 7B disassociated with the implanted framework.
Figure 7D:
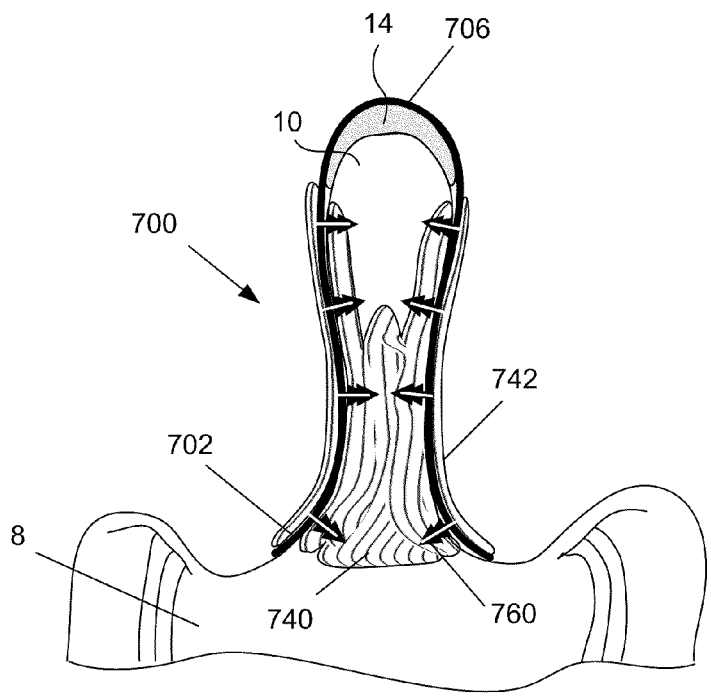
FIG. 7D is a superior view of the framework arranged as shown in FIG. 7C and coated in bone filler.

Referring to FIGS. 7B and 7C, pincers 780 are shown positioning a framework 700 over a target spinous process 10 so that the framework 700 sheaths the spinous process. The framework 700 includes a plurality of anchors 760 extending from one or both of a frame 702 and a mesh 704, as above. The pincers 780 comprises a brace 783 that is urged against the supraspinous ligament 14 and connected with a pivot 788 of the pincers 780. A handle 786 is actuated so that jaws 782,784 of the pincers 780 close around the spinous process 10. The jaws 782,784 preferably are shaped to approximately conform to a shape of the outer surface of the spinous process 10. Referring to FIG. 7C, pins 785 extend from the surface of the jaws 782,784 and are fitted within cavities of the anchors 760. The pins 785 can provide sufficient stiffness to the anchors 760 to resist bending that may otherwise occur due to the flexible or semi-flexible properties of the mesh 704 and/or frame 702 of the framework 700, ensuring that the anchors are appropriately positioned and implanted. The pincers 780 provide a simple, fast, and repeatable method to fixedly connect a framework 700 with a target spinous process 10. Once the framework 700 is satisfactorily positioned, the jaws 782,784 can be separated from the framework 700 and the pincers 780 removed from the implantation site. Referring to FIG. 7D, bone filler 742 can be applied to the outer surface of the spinous process 10 so that the bone filler 742 contacts and/or penetrates the mesh 704 of the framework 700 to form a substantially integral structure supporting the spinous process 10.

Figure 8A:
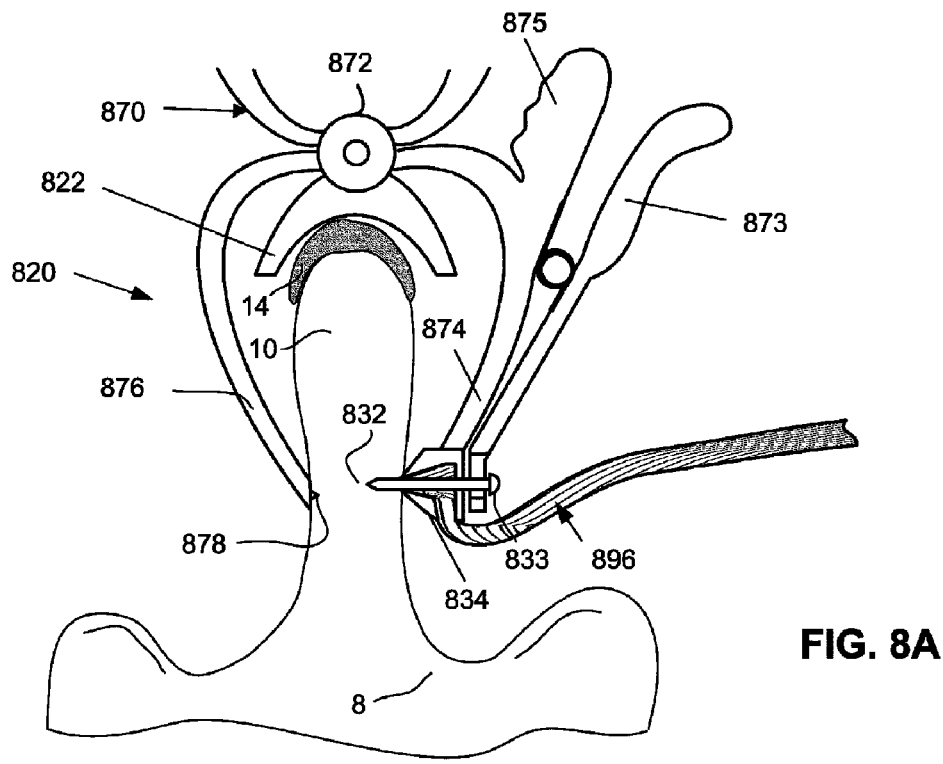
FIG. 8A is a superior view of a bone filler injection tool usable with another embodiment of a system and method positioned over a target spinous process.
Figure 8B:
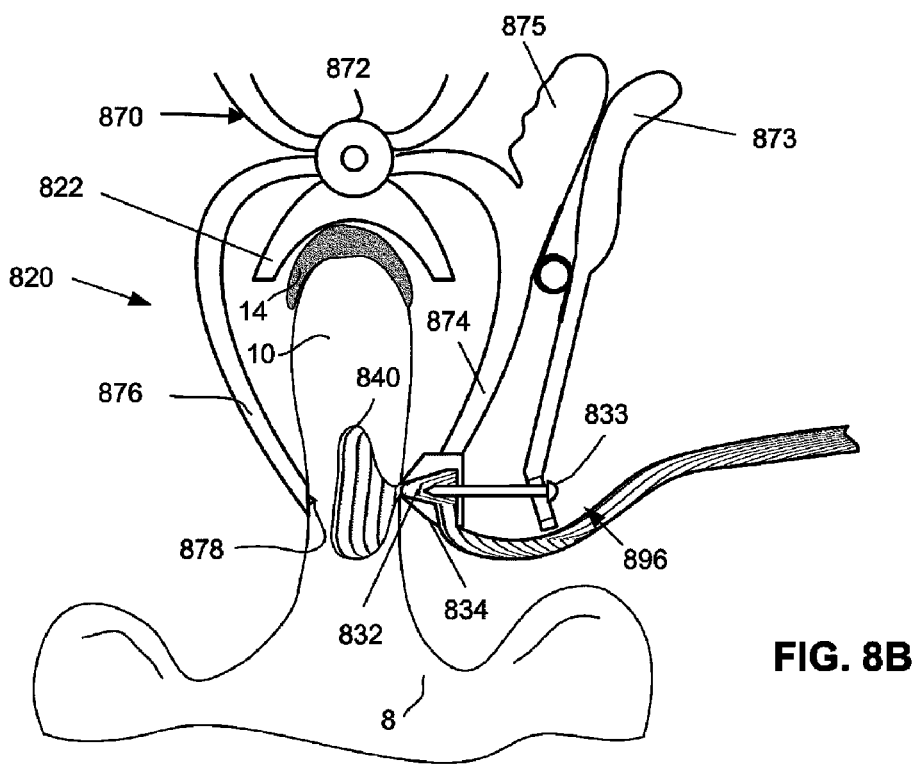
FIG. 8B is a superior view of the bone filler injection tool of FIG. 8A actuated to release bone filler.

FIGS. 8A and 8B illustrate a further embodiment of a system and method of reinforcing one or more spinous processes in accordance with the present invention that can be used with frameworks and methods of sheathing frameworks as shown in FIGS. 3D and 7B-7D. FIG. 8A is a superior view of a guide clamp 820 comprising an integrally connected awl 832 and injection port 834. The awl 832 extends from the injection port 834 and can be retracted by way of a trigger 873 that is connected with a grip 875 extending from a second arm 874 by a spring. As the trigger 873 is urged toward the grip 874, the head 833 of the awl 832 is urged away from the spinous process and the awl 832 is withdrawn so that bone filler 840 can enter the spinous process from a bone filler source 896 connected with the injection port 834. The bone filler source 896 can include a flexible tube attached to the injection port 834 at one end and a syringe (not shown) attached to the flexible tube on the other end containing the bone filler. The guide clamp 820 further comprises a brace 822 that is urged against the supraspinous ligament 14 and connected with a pivot 872. A first arm 876 is clamped in position (by way of the handle 870) on one side of a target spinous process 10 with a spike 878 for resisting slippage while the second arm 874 closes over and against an opposite side of the spinous process 10 with the awl 832 penetrating the spinous process 10. The guide clamp 820 can be used repeatedly at multiple injection sites along the spinous process 10. It may be desirable to have the brace 822 adjust relative to the injection port to allow the guide clamp 820 to be positioned at multiple different distances from the lamina 8 while being positioned against the supraspinous ligament 14. Alternatively, the guide clamp 820 can be one of a set of guide clamps 820 having varying sized awls 832 and first arm 876 and second arm 874 lengths. A user can follow a prescribed program of bone filler injection, using the guide clamps of the set in a prescribed fashion until each has been used.

Figure 9B:
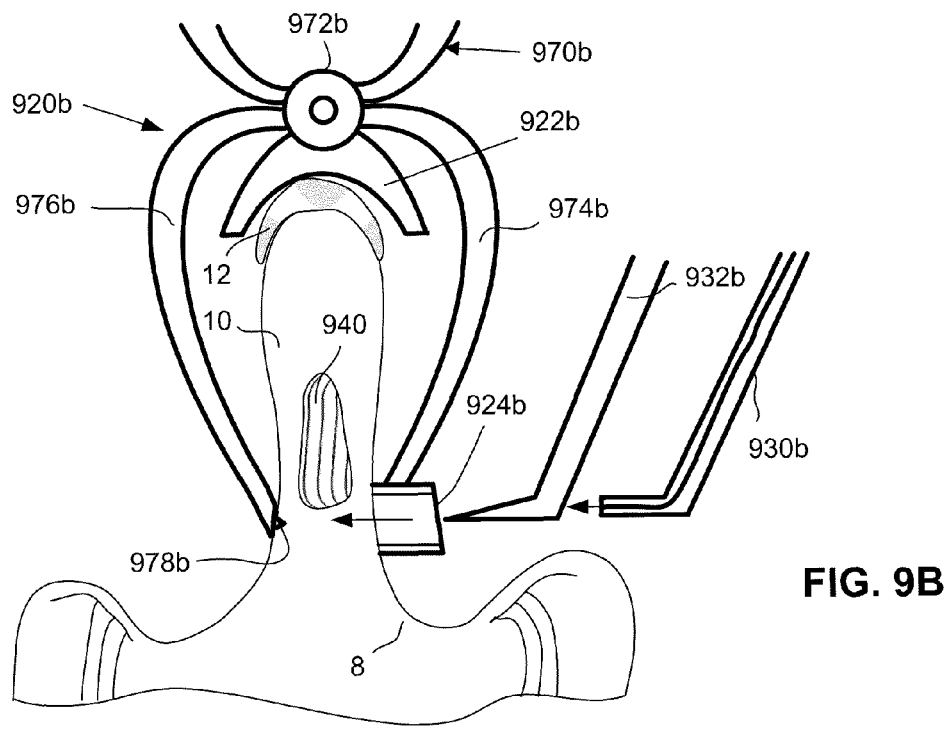
FIG. 9B is a superior view of a second jig of the series of jigs usable with another embodiment of a system and method positioned over a target spinous process.

FIGS. 9A and 9B illustrate a further embodiment of a system and method of reinforcing one or more spinous processes in accordance with the present invention comprising a set of clamping tools for guiding piercing and/or filling tools. FIG. 9A is a superior view of a guide clamp 920a comprising a brace 922a that is urged against the supraspinous ligament 14 and connected with a pivot 972a. A first arm 976a is clamped in position (by way of the handle 970) on one side of a target spinous process 10 with a spike 978a for resisting slippage while a second arm 974a closes over and against an opposite side of the spinous process 10 with slots 924a providing a template for an awl 932a and cannula 930a positioned a prescribed distance from the lamina 8. Alternatively, the cannula 930a can include a bevelled distal end capable of piercing the bone as well as depositing bone filler 940. A series of bone filler injections can be performed at the slots 924a to reinforce the body of the spinous process 10. Once the injections are complete, the guide clamp 920a can be released and removed from the spinous process 10 and at least one additional clamp 920b sized and shaped to be positioned a different distance from the lamina 8 is clamped to the target spinous process 10. A corresponding awl 932b and cannula 930b is inserted in subsequent steps to inject bone filler into the second location along the spinous process.

As will be appreciated systems and methods in accordance with the present invention can include different combinations of individual steps presented herein. For example, the bone filler injection steps described in the embodiments of FIGS. 8 and 9 can be combined with the framework implantation steps of any of the embodiments described herein. Further, the foregoing description of different jig embodiments is not intended to be exhaustive or limit the invention to the precise forms disclosed. Thus, various other jigs can be used as envisioned by one having an ordinary skill in the art having the benefit of this disclosure without deviating from the scope of the invention.

The bone filler injection device described herein can include any commercially available device which is used to inject bone filler into a bone as envisioned by one having an ordinary skill in the art having the benefit of this disclosure. The surgical process used to inject the bone filler into the spine may also be monitored by the surgeon using any real-time imaging techniques, such as an x-ray fluoroscopy. Finally, the bone filler described above can include any appropriate commercially available bone filler as envisioned by one having an ordinary skill in the art having the benefit of this disclosure. In an embodiment, the bone filler can include polymethylmethacrylate (PMMA) or any other appropriate bone cement.

It is to be understood that the method steps described herein can be conducted in any order and/or simultaneously. For simultaneously performed method steps, both the spinous process and the mesh can be infused with bone filler. For example, the bone filler can be injected into the spinous process and simultaneously pass through at least part of the spinous process in order to contact the mesh. Alternatively, injection needles can simultaneously injected bone filler in the spinous process and also into the mesh and the area between the mesh and the spinous process.

While embodiments and applications of this invention have been shown and described, it would be apparent to those skilled in the art having the benefit of this disclosure, that many more modifications than mentioned above are possible without departing from the inventive concepts herein.

The invention claimed is:

1. A method for strengthening a spinous process, comprising:
    positioning a framework over an outer surface of the spinous process, the framework comprising a mesh connected to a frame;
    distributing bone filler over the mesh so that the bone filler contacts the mesh and contacts the spinous process;
    allowing the bone filler to cure along the outer surface;
    positioning a jig at the spinous process over the mesh and bone filler so that a slot through the jig is exposed to a side of the spinous process;
    orienting a cannula so that the cannula is receivable in the slot;
    inserting the cannula into the spinous process through the slot;
    injecting bone filler into the spinous process by way of the cannula;
    terminating the injection when a desired amount of bone filler has been injected into the spinous process;
    removing the cannula from the spinous process; and
    allowing the bone filler to cure within the spinous process.

2. The method of claim 1, wherein the step of distributing bone filler over the mesh is performed simultaneously with injecting bone filler into the spinous process.

3. The method of claim 1, wherein the step of distributing bone filler over the mesh is performed subsequent to injecting bone filler into the spinous process.

4. The method of claim 3, wherein the cannula includes one or more side openings associated with a stop that limits the depth of insertion, the one or more side openings directing bone filler over the mesh.

5. The method of claim 1, wherein the slot is non-circular in shape; and wherein orienting a cannula further includes aligning the cannula having a complementary non-circular shape with the slot.

6. The method of claim 1, further comprising the step of positioning the cannula within the vertebra at a desired location, wherein the desired location is superficial to the vertebral foramen and spinal canal.

7. The method of claim 1, wherein the cannula comprises a stop that limits the depth of insertion.

8. The method of claim 1 wherein the one or more side openings are delivery tubes.

9. The method of claim 1, wherein the jig comprises a brace to contact a supraspinous ligament of the spinous process so that the slot is positioned to direct the cannula to a target location of the spinous process.

10. The method of claim 1 wherein the jig comprises:
    a first arm contacting the mesh and bone filler on one side of the spinous process so as to resist slippage, and
    a second arm contacting the mesh and bone filler on an opposite side of the spinous process, the second arm providing the slot to guide a cannula to a target location.

11. The method of claim 1, further comprising inserting an awl into the slot to create a path for inserting the cannula.

12. The method of claim 1, wherein the step of positioning the jig is performed simultaneously with the step of positioning the framework.

13. The method of claim 1, wherein the framework includes:
a first support contacting one side of the spinous process, the first support including a mesh and a frame; and
a second support contacting an opposite side of the spinous process, the second support including a mesh and a frame;
wherein the first support is connected to the second support by a connecting structure.

14. The method of claim 13,
wherein the frame of the first support, the frame of the second support, and the connecting structure are fabricated from a shape memory material; and
wherein when positioned over the spinous process, the framework assumes a shape that generally conforms to the outer surface of the spinous process.

15. The method of claim 13,
wherein the framework includes anchors extending from the first support and the second support; and
wherein the anchors are inserted into the spinous process to grip the spinous process.

16. The method of claim 15, wherein positioning a framework over an outer surface of the spinous process further includes:
closing a pair of pincers mated with the anchors over the spinous process so that the anchors are rigidly directed into the spinous process; and
disassociating the pair of pincers from the anchors.

17. The method of claim 1, wherein the step of injecting bone filler into the spinous process causes bone filler to contact the mesh.

18. A kit for reinforcing a spinous process, comprising:
a framework positionable over the spinous process, the framework including:
a first support having a frame and a mesh connected with the frame,
a second support having a frame and a mesh connected with the frame, and
a connecting structure connecting the first support to the second support,
wherein when the framework is positioned over the spinous process, the framework sheaths the spinous process;
a jig including a slot extending through the jig so that when the jig is positioned at a spinous process over the first support and the second support, the slot is exposed to a side of the spinous process; and
a cannula receivable in the slot.

19. The kit of claim 18,
wherein the frame of the first support, the frame of the second support, and the connecting structure are fabricated from a shape memory material; and
wherein when positioned over the spinous process, the framework assumes a shape that generally conforms to the outer surface of the spinous process.

20. The kit of claim 18, wherein the cannula comprises a stop that limits the depth of insertion.

21. The kit of claim 18, wherein the cannula includes one or more side openings.

22. The kit of claim 21, wherein the one or more side openings are delivery tubes.

23. The kit of claim 18, wherein the jig comprises a brace to contact a supraspinous ligament of the spinous process so that the slot is positioned to direct the cannula to a target location of the spinous process.

24. The kit of claim 18, wherein the jig further includes:
a brace contacting a supraspinous ligament of the spinous process,
a first arm contacting one side of the spinous process so as to resist slippage, and
a second arm contacting an opposite side of the spinous process, the second arm providing the slot to guide a cannula to a target location.

25. The kit of claim 18, further comprising inserting an awl into the slot to create a path for inserting the cannula.

26. A method for strengthening a spinous process, comprising:
positioning a framework over an outer surface of the spinous process, the framework comprising a mesh connected to a frame;
distributing bone filler over the mesh so that the bone filler contacts the mesh and contacts the spinous process;
allowing the bone filler to cure over the outer surface;
positioning a jig over the framework so that a brace of the jig is positioned at the supraspinous ligament of the spinous process;
actuating the jig so that a first arm contacts the framework on one side of the spinous process to resist slippage and a second arm contacts the framework on an opposite side of the spinous process;
penetrating the opposite side of the spinous process with an awl extending from the second arm;
retracting the awl from the opposite side without moving the second arm so that an injection port of the second arm is exposed to the penetrated spinous process;
injecting bone filler into the spinous process by way of the injection port;
terminating the injection when a desired amount of bone filler has been injected into the spinous process;
removing the jig from the spinous process; and
allowing the bone filler to cure within the spinous process.

27. The method of claim 26, wherein the step of distributing bone filler over the mesh is performed simultaneously with injecting bone filler into the spinous process.

28. The method of claim 26, wherein the step of distributing bone filler over the mesh is performed subsequent to injecting bone filler into the spinous process.

* * * * *